United States Patent [19]

Burton et al.

[11] Patent Number: 5,464,820

[45] Date of Patent: Nov. 7, 1995

[54] SPECIFIC INHIBITORS OF TISSUE KALLIKREIN

[75] Inventors: James Burton, Jamaica Plain; Zhengxin Dong, Somerville; Timothy B. Frigo, Watertown, all of Mass.

[73] Assignee: The University Hospital, Boston, Mass.

[21] Appl. No.: 79,812

[22] Filed: Jun. 22, 1993

[51] Int. Cl.$^6$ .......................... A61K 37/00; A61K 37/02; C07K 5/00; C07K 7/00
[52] U.S. Cl. ................................ 514/16; 514/17; 514/18; 530/329; 530/331
[58] Field of Search .................................. 530/331, 329; 514/16, 17, 18

[56] References Cited

U.S. PATENT DOCUMENTS

| | | | |
|---|---|---|---|
| 4,818,748 | 4/1989 | Bender et al. | 514/16 |
| 4,835,253 | 5/1989 | Burton | 530/330 |

OTHER PUBLICATIONS

Everest et al. J. Med. Microbiol. vol. 38 p. 316 (1993)–abstract only.
John M. Stewart et al., "Design of Bradykinin antagonists", Marshal, GR Peptides: Chemistry and Biology (1988) ESCOM: Leiden, pp. 433–437.
George Triadafilopoulos et al., "Differential Effects of Clostridium difficile Toxins A and B on Rabbit Ileum" Gastroenterology 1987; 93:273–9.
Hideki Okunishi et al., "The Design of Substrate Analogue Tissue Kallikrein Inhibitors", Hypertension Supplement I, vol. 8, No. 4, Apr. 1986, pp. 1–114–118.
R. W. Colman et al., "Kallikrein–Kinin System in Pathologic Conditions", Bradykinin, Kallidin and Kallikrein Supplement, E. G. Erdos editor Springer–Verlag, New York 1979, pp. 569–607.
R. Vogel, "Kallikrein Inhibitors", Bradykinin, Kallidin and Kallikrein Supplement, E. G. Erdos editor Springer–Verlag, New York 1979, pp. 163–225.
Hideki Okunishi et al., "In vivo inhibition of tissue kallikreins by kininogen sequence analogue peptides", In: Abe K. Kinins V. Plenum, New York 1988; In Press, 6 pp.

Hideki Okunishi et al., "Specificity of Substrate Analogue Inhibitors of Human Urinary Kallikrein", Blood Pressure Council Suppl. I Hypertension, vol. 7, No. 3, May–Jun. 1985, pp. I–72–75.
Timothy S. Gaginella et al., "Kinins as mediators of intestinal secretion", Editorial Review, 1989, the American Physiological Society, pp. G1–G15.
C. Pothoulakis, "Abstract" presented at Barcelona, Jul. 19–24, 1993, United European Gastroenterology Week, Inhibition of Intestinal Effects of Clostridium Difficile Toxin a By a Specific Substance P Antagonist.
Hideki Okunishi et al., "In Vivo Assay Of Specific Kallikrein Inhibitors", Vasodepressor Hormones, 1987 Birkhauser Verlag Basel, pp. 381–390.
J. Burton et al., Poster presented at Boston University; Evans Research Day, Sep. 1993, "Effect of the Kallikrein Antagonist on Clostridium Difficile Toxin a Induced Intestinal Secretion".
George Triadafilopoulos et al., "Comparative Study of Clostridium difficile Toxin A and Cholera Toxin in Rabbit Ileum", Gastroenterology, 1989; 97:1186–92.
Milind S. Deshpande et al., "Mapping the Binding Site of Tissue Kallikrein: Preparation and Testing of All Possible Substrate Analog Inhibitors Homologous with the Sequence of Kininogen between Ser$^{388}$ and GLn$^{392}$". Reprinted from Journal of Medicinal Chemistry, 1992, vol. 35, No. 17, pp. 3095–3102.
J. Garcia Leme, "Bradykinin–System", Inflammation, 1978, Chapter 14, pp. 464–522.

*Primary Examiner*—Jill A. Warden
*Assistant Examiner*—Sheela J. Huff
*Attorney, Agent, or Firm*—Baker & Botts

[57] ABSTRACT

The invention is directed to substrate analogs which are specific for tissue kallikrein. These analogs contain a sequence which corresponds to at least positions 388 to 390 of human kininogen, and which has a 4-aminophenylalanine (Phe(4NH$_2$)), or a structurally or functionally similar residue, corresponding to position 389. These substrate analogs are useful in compositions and methods for the treatment or prevention of biological activities associated with tissue kallikrein including inflammation, the regulation of blood flow, the regulation of proenzyme activity through processing, shock, hypotension, vascular leakage, and the perception of pain.

20 Claims, 8 Drawing Sheets

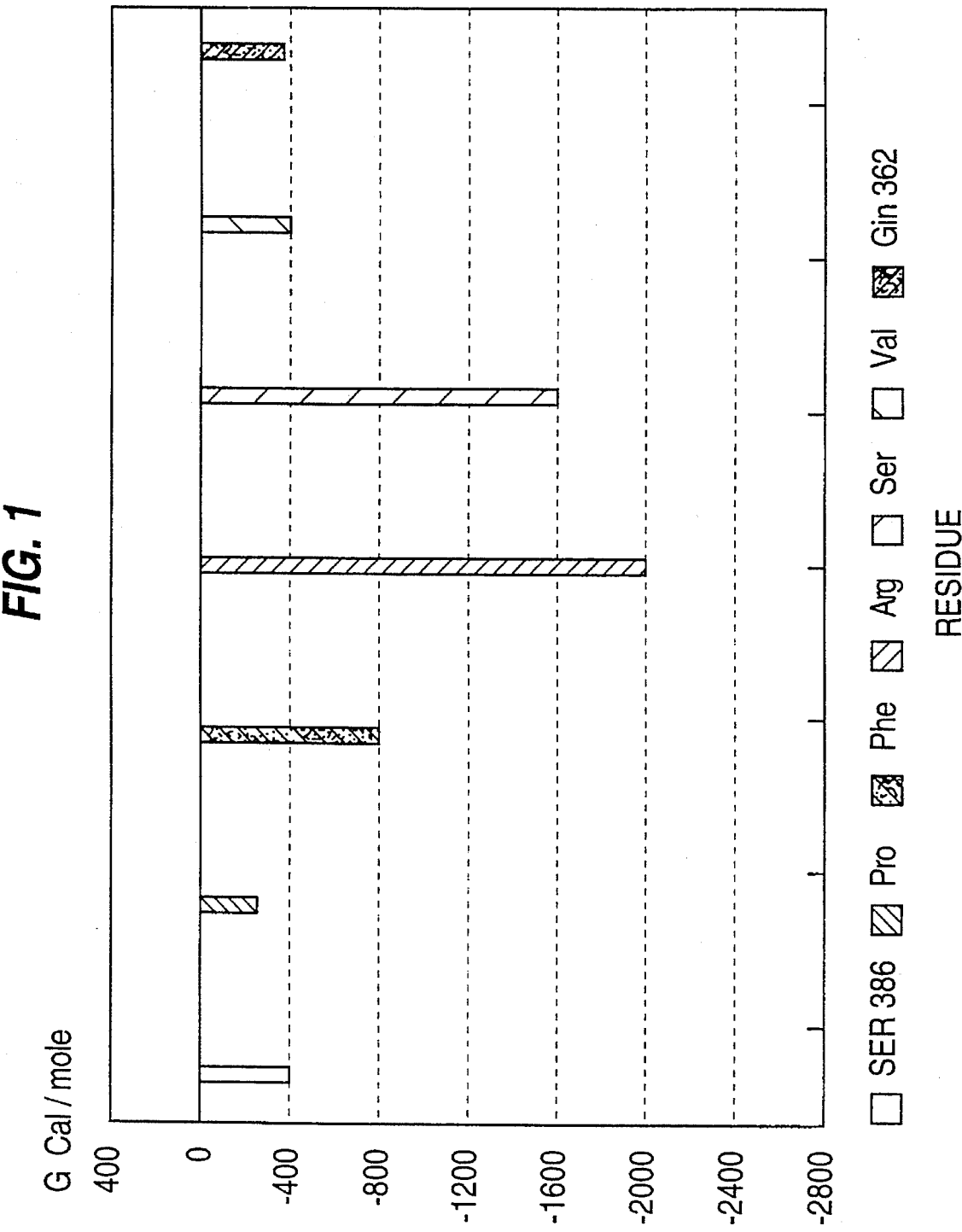

 FIG. 3D D-Abu
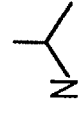 FIG. 3C D-Ala
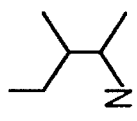 FIG. 3B Gly
FIG. 3A Pro
 FIG. 3H D-aIle
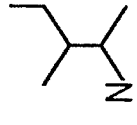 FIG. 3G D-Ile
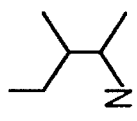 FIG. 3F D-Val(3Me)
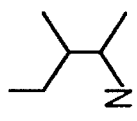 FIG. 3E D-Val
 FIG. 3K D-Adg
 FIG. 3J D-Chg
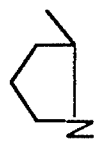 FIG. 3I D-Apn(3Et)
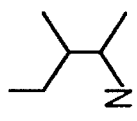

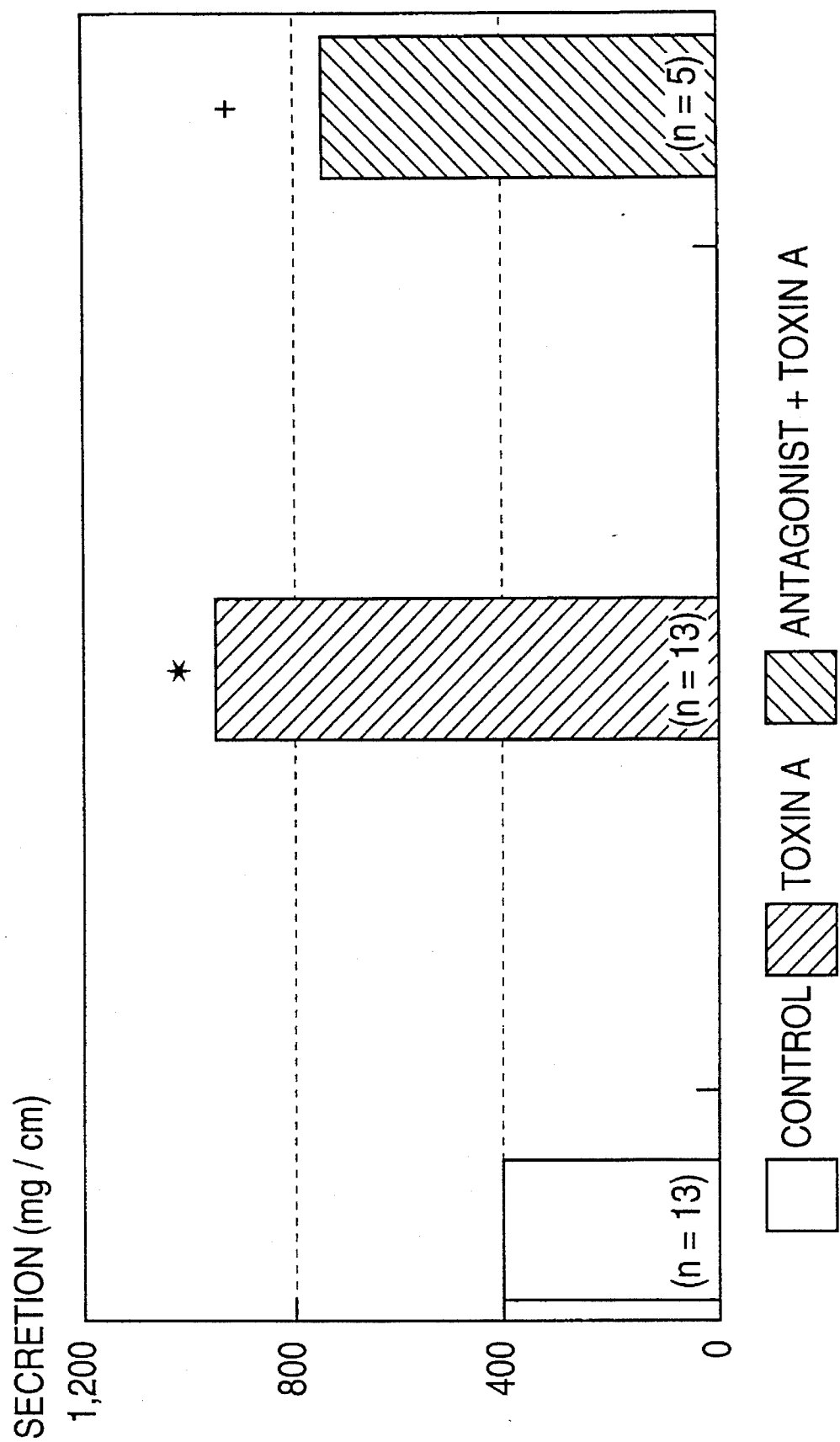

SPECIFIC INHIBITORS OF TISSUE KALLIKREIN

BACKGROUND OF THE INVENTION

1. Field of the Invention

This invention relates to substrate analog inhibitors of tissue kallikrein which comprise peptide sequences corresponding to the partial amino acid sequence of kininogen. These substrate analogs specifically inhibit the activity of tissue kallikrein. Administration of these substrate analogs to a patient affects the biological processes associated with tissue kallikrein function including inflammation, edema, the regulation of blood flow, and the regulation of proenzyme activity through processing. In turn, this can control shock, hypotension and the perception of pain.

2. Description of the Background

Kallikreins are substrate specific proteolytic enzymes which are found in nearly xty years ago when Frey and Kraut observed that intravenous injections of human urine into dogs had hypotensive properties (E. K. Frey and H. Kraut, Arch. Exp. Pathol. Pharmakol. 133:1, 1926). These investigators determined that a specific substance was responsible. This substance was identified in human pancreatic cells and was termed "kallikrein," the greek synonym for pancreas ("kallikreas"; H. Kraut et al., Physiol. Chem. 189:97, 1930).

The kallikreins are serine proteases, a group of enzymes wherein each contains an active serine residue. About fifty serine proteases have been identified to date and there are likely to be many more (Bradykinin, Kallidin and Kallikrein, E. G. Erdos editor, Springer-Verlag, New York, N.Y., 1979).

There are two principle categories of kallikreins, the plasma kallikreins (Enzyme Commission of the International Union of Biochemistry Committee on Nomenclature or "EC" Number 3.4.21.34), and the tissue kallikreins (EC number 3.4.21.35), also referred to as glandular or organ kallikreins. In some animals, notably the rat and mouse, gene duplication has led to the appearance of many kallikreins. In higher animals, the number is more restricted. Plasma kallikrein, with a molecular weight of about 100,000 daltons, circulates in the blood in a precursor form called kallikreinogen or prekallikrein. Prekallikrein is converted to its activated form by factor XII of the blood clotting cascade, also called the Hageman Factor. The principle functions of plasma kallikrein are in the activation of the blood clotting and compliment enzyme cascades. In the clotting process, factor XII activates plasma kallikrein which, besides activating additional prekallikrein, activates intrinsic blood coagulation. Plasma kallikreins are also involved with the activation of the complement cascade which entails upwards of a dozen different proteases.

Tissue kallikreins have been isolated from saliva, intestine, lung, brain, plasma, and a variety of other bodily cells and fluids. The well-known types were isolated from urine and the pancreas. Biochemical studies reveal that tissue kallikreins are heat-stable glycoproteins which consist of a single amino acid chain having a molecular weight of 27,000 to 40,000 daltons. Both the amino acid sequence and the tertiary conformation of some kallikreins are known. Substrates of tissue kallikrein include procollagenase, kininogen, proinsulin, prorenin, BAM 22P, atrial naturietic factor, low density lipoprotein, atriopeptigen, and tissue plasminogen activator. These compounds are each processed or activated by proteolysis. Kininogen, in particular, requires kallikrein activity. Cleavage products of kininogens are referred to as kinins. Kinins are hormones which fall into the group called autocoids. Traditional hormones are made by a particular gland and act at sites distant from that gland. In contrast, autocoids are made locally, and bind and act locally.

Kinins liberated from kininogen bind to kinin receptors. It is generally believed that there are several types of kinin receptors. The major kinin binding structures that have been identified on normal cells are the $B_1$, $B_2$ (the classic kinin receptor), $B_3$, $B_4$ and $B_5$ surface receptors. These receptors can also bind heterologous molecules (kinin analogs) found in bee and snake venom. A series of synthetic peptides based on the structure of bradykinin have been shown to block kinin receptors, and particularly the $B_2$ receptor. These kinin analogs are not closely related to substrate analog inhibitors.

Numerous functions have been attributed to kinins including increased chloride transport across plasma membranes, the activation of phospholipase $A_2$, and the release of interleukins, substance P, prostaglandins, and tumor necrosis factor. Primary roles for kinins have been shown to include the regulation of blood flow, blood pressure and sodium/water balance. Kinins have also been implicated in the sensation of pain, rheumatoid arthritis, allergic reactions, and vascular leakage (edema) from rhinitis. Clinical evidence indicates that administration of angiotensin I converting enzyme inhibitors (ACE), a known potentiator of kinin, produces a decrease in mean arterial pressure in humans. This correlate better with increases in circulating levels of kinins than with decreases in levels of circulating angiotensin II.

Tissue kallikreins are relatively specific for cleavage of kininogen, a hepatic-derived protein which circulates in the blood in two forms, a low molecular weight form of about 50,000 to 60,000 daltons (LMW-kininogen), and a high molecular weight form of about 120,000 daltons. Plasma kallikreins prefer to cleave the high molecular weight form, whereas tissue kallikreins prefer the low molecular weight form. Tissue kallikrein cleaves at two types of peptide bonds in LMW-kininogen, a methionine-lysine bond and an arginine-serine bond. Tissue kallikrein is thought to first cleave the arginine-serine peptide bond and then the methionine-lysine peptide bond to release Lys-bradykinin (Kallidine). Kallidine may be further processed by various amino peptidases into the nonapeptide, bradykinin.

Kallidin has been termed the "master hormone of inflammation" and one of the major roles of the tissue kallikreins in the body is in the regulation of inflammation. Inflammation is a multimediated process involving a large number of endogenous substances including the kinins. The kinins involved in inflammation include bradykinin, Lys-bradykinin or kallidin, and Met-Lys-bradykinin. They have the properties of being able to contract most smooth muscle preparations, but relax the muscles of the rat duodenum. Each of these peptides display similar actions, but with different potencies.

Trauma and local inflammation leads to an increased synthesis by the liver of certain plasma proteins, the acute phase reactants. Kininogen and kininogenase belong in this category of substances. It has been observed that total kininogen levels change in response to certain pathological conditions pointing to a possible involvement of kinin in the pathological process. However, local conditions can induce a continuous formation of kinins in the injured area. Therefore, it is more important to look at release of kinins in the extravascular tissues from extravasated plasma proteins in order to demonstrate the participation of these substances in inflammation.

Bradykinin, kallidin and related polypeptides are found in high concentrations at the sites of physiologically traumatic events. As trauma usually produces inflammation, a possible connection was investigated. Bradykinin applied to skin vessels of anaesthetized rats produced a marked increase in flow through the capillary vessels. Venules were dilated to a proportionately greater extent than were arterioles. Amounts less than one nanogram produced only vasomotor changes. Amounts of greater than one nanogram produced vasomotor changes were much more protracted and an increased permeability developed in the post capillaries and the collecting venules which was independent of histamine release. There was also a tendency for blood vessels to clump leading to a complete stasis of blood flow in these vessels.

Pain in the inflammatory process is a result of the release of algogenic or other substances which sensitize the pain receptors or P-fibers. Mechanical disruption is thought to play an important part in the development of pain, but pain receptors are not mechano-sensitive and pain and swelling are not related in a constant manner. Pain receptors are essentially chemoreceptive and found in the visceral and cutaneous areas of the body. Injury and regional ischaemia, including thermal injury, chemical injury, electrical injury, local trauma, and localized or systemic infection, leads to the disintegration of circulating and fixed cells. These cells release lysosomal proteases, produce localized acidosis, stimulate the production of prostaglandins and vasoactive amines, and activate the kinin system. All these conditions favor the stimulation and sensitization of pain receptors.

Involvement of kinins and kallikreins in inflammation produces vasodilation, increased vascular permeability, pain, and edema. Understanding the importance of tissue kallikrein in these biological processes depends on development of tissue kallikrein inhibitors which can be used in vivo. Specific inhibitors would reduce or decrease the undesirable effects of, for example, inflammation. Specific inhibition of tissue kallikrein would not inhibit the action of either the blood coagulation or complement cascades, either of which would be unwanted consequences of inhibition of plasma kallikrein.

In many instances, depletion of the available pool of kininogen reduces the signs and symptoms of inflammation. Kinin destroying enzymes, such as carboxypeptidase-B, has also been shown to interfere with the development of inflammation.

The kinin receptor blockers have been extremely valuable for the study of the biological effects of kinins. However, these compounds do not identify the source of kinins, making it difficult to know whether tissue or plasma kallikrein is responsible for a specific physiological effect. The receptor blockers also function as partial agonists in some systems, complicating the analysis of results from in vivo tests. Protease inhibitors such as aprotinin and its fragments, benzamidine, aromatic diamidines, and peptides containing a chloromethyl ketone group, do not appear to be specific for tissue kallikrein.

The key issue in the successful design of tissue kallikrein inhibitors is specificity. The progenitor serine protease which gave rise to tissue kallikrein also led to numerous other serine proteases. Tissue kallikrein and its family of related enzymes still share many features, including the ability to hydrolyze similar substrates and to be inhibited by related compounds such as aprotinin and the benzamidines. To avoid non-specific effects, tissue kallikrein inhibitors should not block other proteases.

A theory to explain specificity of proteases for their substrates has been developed (M. S. Deshpande and J. Burton, J. Med. Chem. 35:3094–3102, 1992). This theory points to a method of preparing specific inhibitors of a variety of proteases including tissue kallikrein. It is based on the observation that highly homologous serine proteases function specifically in vivo. Some factors makes it possible for proteases to selectively cleave substrates which are commingled in the blood such that each enzyme performs a single function.

The specificity of the interaction must reside in the match between the amino acid sequences of the cleavage site of the substrate and the active site of the enzyme. It has been shown that the species specificity of renin for angiotensinogen was mimicked by relatively short peptides from the cleavage site of the substrate (J. Burton and T. Quinn, Biochim. Biophys. Acta 952: 9–12, 1986). Subsequently, oligopeptides which encompass the cleavage site of kininogen were demonstrated to specifically bind to tissue kallikrein and much less well to related proteases (H. Okunishi et al., Hypertension 7:72–75, 1985).

The cleavage site can be depicted as a series of peptides numbered according to proximity from a central arginine residue. Beginning with arginine and continuing to the left, toward the amino terminus, residues are designated $P_1$, $P_2$, $P_3$, etc. Residues to the right of arginine, toward the carboxy terminus, are designated $P_1'$, $P_2'$, $P_3'$, etc. (SEQ. ID. NO. 4):

| 386 | | 388 | | | 390 | | 392 | (amino acid position) |
|---|---|---|---|---|---|---|---|---|
| Ser- | Pro- | Phe- | Arg- | | Ser- | Val- | Gln- | (bovine kininogen) |
| $P_4$ | $P_3$ | $P_2$ | $P_1$ | ↑ | $P_1'$ | $P_2'$ | $P_3'$ | |

The premise that specificity resides in residues around the cleavage site (↑) has been quantified by recent work with a series of kininogen peptides which bind to tissue kallikrein. The energy ($\Delta\Delta G$) that each amino acid in the sequence (SEQ. ID. NO. 4) Ser-Pro-Phe-Arg-Ser-Val-Gln contributes to binding of tissue kallikrein is depicted in FIG. 1. Eighty percent of the energy of interaction comes from the Phe-Arg-Ser sequence at the core of the inhibitor (M. S. Deshpande et al., J. Med. Chem. 35:3094–3102, 1992). Tissue kallikrein is inhibited by peptides which are homologous with the amino acid sequence of the substrate around the cleavage site.

Tissue kallikrein and plasma kallikrein appear to recognize overlapping, but somewhat different parts of the kininogen molecule. Preliminary experiments on the interaction of the kininogen peptides with plasma kallikrein show that most of the binding energy for the kininogen-plasma kallikrein interaction may be attributed to the arginine ($P_1$) and glutamine ($P_3'$) residues (G. Lalmanach et al., Proc. 13th Am. Pept. Symp., Edmonton, Alberta, Canada, June 1993). Neither the phenylalanine residue at $P_2$ nor the serine residue at $P_1'$ appear to be important in the interaction between the substrate and this enzyme. Despite these distinctions, to date, no specific inhibitors of tissue kallikrein have been identified.

SUMMARY OF THE INVENTION

The present invention overcomes the problems and disadvantages associated with current strategies and designs and provides compositions and methods comprising substrate analogs containing peptide sequences which correspond to the amino acid sequence of kininogen. These substrate analogs specifically inhibit the activity of tissue kallikrein, affecting the biological and physiological processes associated with tissue kallikrein including inflammation, the regulation of blood flow, the processing and activation of proenzymes, shock, hypotension and the perception of pain.

One embodiment of the invention is directed to peptides which specifically inhibit the activity of tissue kallikrein. These peptides have an amino acid sequence corresponding to at least a portion of the kininogen protein from amino acid positions 388 to 390 (Phe-Arg-Ser). They prevent kininogen binding and cleavage by the serine protease, tissue kallikrein. The peptide sequence further comprises the modified amino acid, 4-aminophenylalanine (Phe(4$NH_2$)), corresponding to position 389 of kininogen and provides, at least in part, the specificity attributed to the peptide. In addition, this modified amino acid is uncharged at physiological pH (7.4). It replaces the amino acid arginine, which is charged and polar, thus reducing the overall net charge of the substrate analog. Alternatively, the invention is also directed to nucleic acid sequences which express peptides containing the desired sequence, including nucleic acid sequences associated with efficient expression.

Another embodiment of the invention is directed to compositions containing peptides, as described above, that specifically inhibit the activity of tissue kallikrein. These compositions are useful for the treatment or prevention of biological processes associated with tissue kallikrein function and can be administered to a patient locally, to treat a certain area of the body, or systemically for a wider distribution and effect. The reduced overall net charge of the peptide allows for the production of compositions which are orally bioavailable.

A further embodiment of the invention is directed to methods for the use of these peptides and compositions for the treatment of harmful effects associated with the activation of kininogen by tissue kallikrein including inflammation, increased blood flow and proenzyme activity, shock, hypotension, vascular leakage, and the perception of pain.

Other embodiments and advantages of the invention are set forth, in part, in the description which follows and, in part, will be obvious from this description or may be learned from the practice of the invention.

DESCRIPTION OF THE DRAWINGS

FIG. 1 Graph of ΔΔG values for the interaction of amino acid residues in the substrate analog inhibitors and tissue kallikrein.

FIG. 3 Structures of amino acid analogs substituted at $P_3$.

FIG. 8 Models of the absorption of peptides.

DESCRIPTION OF THE INVENTION

Figure 2A:
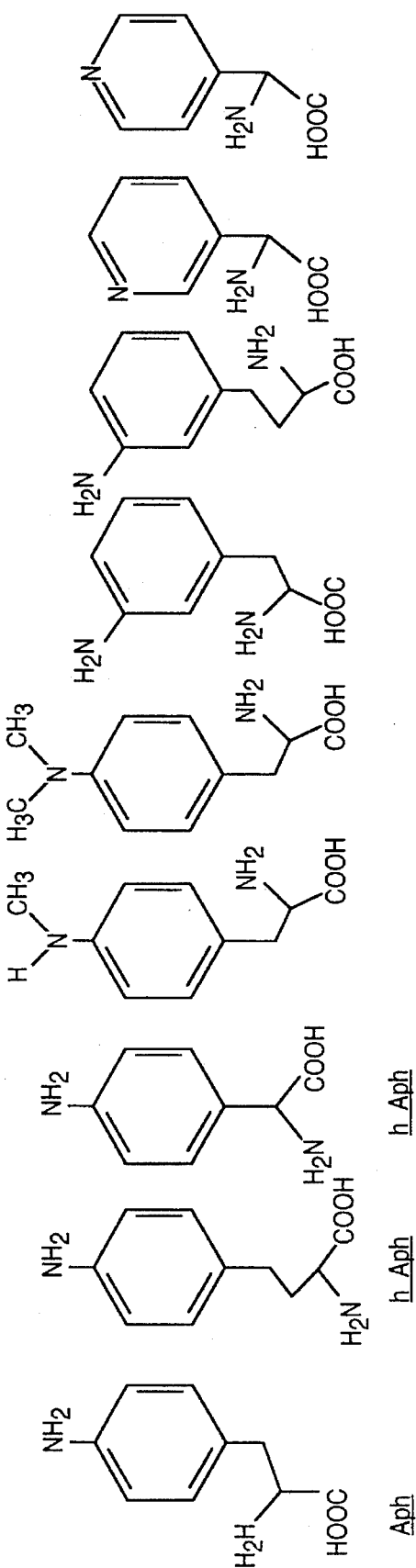
FIG. 2 Structures of amino acid analogs which may substitute for Arg in a substrate analog of the kininogen platform sequence (positions 389).

To achieve the objects and in accordance with the purpose of the invention, as embodied and broadly described herein, the present invention comprises peptides, compositions, and methods for the prophylaxis and treatment of biological and physiological processes associated with tissue kallikrein.

To be specific, the binding energy of a tissue kallikrein inhibitor based on the substrate, or substrate analogue, should mimic the binding profile of the natural substrate which is cleaved specifically in vivo. The $P_2$ (Phe), $P_1$ (Arg), and $P_1'$ (Ser) residues contribute 15%, 40%, and 25%, respectively, of the total binding energy (FIG. 1). For specific plasma kallikrein inhibitors most of the binding energy is at the $P_1$ and $P_4'$ residues.

If multiple residues in a substrate analogue inhibitor contribute to specificity, most transition state analogs are probably doomed to fail due to an inherent lack of specificity. Incorporation of a transition state analogue into the kallikrein inhibitors at the arginine residue ($P_1$) increases binding 2–3 orders of magnitude. The increase in binding is due to modification of a single residue which is recognized by many different proteases. The transition state residue at this position increases the binding to all of these enzymes and overcomes any specificity due to other residues in the original sequence.

Specific inhibitors of tissue kallikrein incorporate amino acid analogs at each position in such a way that the percentage of the total binding energy that each residue contributes is similar to that found in the relatively specific substrate analog inhibitors. To incorporate a transition state element at $P_1$ which increases binding by two orders of magnitude, this modification will be balanced by alterations at $P_2$ and $P_1'$ which create similar improvements in affinity. Maintaining the overall binding profile of the inhibitor to the enzyme should maintain the selectivity shown in the interaction of the enzyme with its natural substrate. These considerations can limit the affinity that an inhibitor may have and still be specific. If replacing a residue with a sequence with various analogs increases ΔΔG at the position by a set amount, increases in binding at other positions may only be increased a proportional amount to still maintain the desired profile.

One embodiment of the invention is directed to substrate analogs of tissue kallikrein. These substrate analogs comprise a peptide with an amino acid sequence corresponding to positions 388 to 390 of tissue kallikrein. Peptides may be made synthetically, genetically by recombinant engineering techniques, such as by cloning and expressing of a nucleic acid sequence, or purified from natural sources such as a bacterial, fungal or cellular extracts. The structure, chemical, physicochemical, nomenclature and analytical aspects of amino acids are described in Chemistry of the Amino Acids (J. P. Greenstein and M. Winitz editors, John Wiley & Sons, New York, N.Y., 1961, reprinted 1984), which is hereby specifically incorporated by reference. The peptides are comprised of modified and/or unmodified amino acids which include the naturally occurring amino acids, the non-naturally occurring (non-coding) amino acids, synthetically made amino acids, and combinations thereof. The naturally occurring amino acids include glycine (Gly), the amino acids with alkyl side chains such as alanine (Ala), valine (Val), leucine (Leu), isoleucine (Ile), and proline (Pro), the aromatic amino acids phenylalanine (Phe), tyrosine (Tyr) and tryptophan (Trp), the amino acid alcohols serine (Ser) and threonine (Thr), the acidic amino acids aspartic acid (Asp) and glutamic acid (Glu), the amides of Asp and Glu, asparagine (Asn) and glutamine (Gln), the sulfur-containing amino acids cysteine (Cys) and methionine (Met), and the basic amino acids histidine (His), lysine (Lys), and arginine (Arg). The non-naturally occurring amino acids include, for example, ornithine (Orn), norleucine (Nle), citralline (Cit), homo-citralline (hCit), desmosine (Des), and isodesmosine (Ide).

Modified amino acids include derivatives and analogs of naturally and non-naturally occurring, and synthetically produced amino acids. Such amino acid forms have been chemically modified such as, for example, by halogenation of one or more active sites with chlorine (Cl), bromine (Br), fluorine (F), or iodine (I), alkylation with a carbon containing group such as a methyl (Me), ethyl (Et), butyl (Bu), amino ($NH_2$ or $NH_3$), amidino (Am), acetomidomethyl (Acm), or phenyl (Ph) group, or by the addition of a phosphorous (P), nitrogen (N), oxygen (O) or sulfur (S) containing group. Modifications may also be made by, for example, hydration, oxidation, hydrogenation, esterification, or cyclization of another amino acid or peptide, or of a precursor chemical. Examples include the amino acid hydroxamates and decarboxylases, the dansyl amino acids, the polyamino acids, and amino acid derivatives. Specific examples include gamma amino butyric acid (GABA), hydroxyproline (Hyp), aminoadipic acid (Aad) which may be modified at the 2 or 3 position, o-aminobutyric acid (Aab or Abu), selenocysteine ($SeCys_2$), tert-butylglycine (Bug or tert-BuGly), the N-carbamyl amino acids, the amino acid methyl esters, amino-propionic acid (or β-alanine; 13-Ala), adamentylglycine (Adg), aminocaproic acid (Acp), N-ethylasparagine (Et-Asn), allo-hydroxylysine (aHyl), allo-isoleucine (aIle), phenylglycine (Phg), pyridylalanine (Pal), thienylalanine (Thi), α-Δ-aminobutyric acid (Kbu), α-β-diaminopropionic acid (Kpr), 1- or 2-naptithylalanine (1Nal or 2Nal), orthofluorophenylalanine (Phe(o-F)), N-methylglycine (MeGly), N-methyl-isoleucine (MeIle), N-methyl-valine (MeVal), 2-amino-heptanoic acid (Ahe), 2- or 3-amino-isobutyric acid (Aib), 2-amino-pimellic acid (Dbu), 2-2'-diaminopimellic acid (Dpm), 2,3-diaminopropionic acid (Dpr), and N-ethylglycine (EtGly). Chemically produced non-coded amino acids include, for example, phenylglycine (Ph-Gly), cyclohexylalanine (Cha), cyclohexylglycine (Chg), and 4-amino phenylalanine (Phe(4NH$_2$) or Aph). Modified amino acids may also be chemical structures which are not amino acids at all, but are actually classified as another chemical form such as an alkyl amine, a saccharide, a nucleic acid, a lipid, a fatty acid or another acid. Any of the modified or unmodified amino acids which comprise the peptide may be in the D- or L-conformations or comprise one, two or more tautomeric or resonance forms. All amino acids disclosed herein are in the L-conformation unless otherwise indicated.

Preferably, the peptides of the invention are organically synthesized, such as by solid phase peptide synthesis as described in *The Practice of Peptide Synthesis* (M. Bodanszky and A. Bodanszky editors, Springer-Verlag, New York, N.Y. 1984), and *Principles of Peptide Synthesis* (M. Bodanszky editor, Springer-Verlag, New York, N.Y. 1984), which are both hereby specifically incorporated by reference. Boc-amino acids, blocked amino acid precursors, are coupled manually or by means of an automated synthesizer. After synthesis, the peptides are purified to homogeneity, if necessary, by, for example, gel filtration and high-pressure liquid chromatography (HPLC), and characterized by, for example, thin layer chromatography (TLC), HPLC, specific activity, and amino acid composition. Preferably, the peptides are stable at room temperatures and do not decompose under physiological conditions. Salts, buffers, stabilizing compounds, and antibacterial, anti-viral or antifungal agents may be added as necessary.

An alternative embodiment of the invention is directed to DNA or RNA sequences which express the peptide sequences. These nucleic acids may comprise suitable promoters and other sequences necessary for efficient transcription as well as any sequences necessary for efficient translation. Such constructs are well-known to those skilled in the art. Peptide sequences may be purified from cloned bacterial extracts, transformed eukaryotic extracts, or processed from larger precursor peptides using selected or endogenous proteases of the system.

Peptides of the invention are relatively small and preferably less than about twenty amino acids in length, more preferably less than about ten amino acids, and even more preferably two, three four, five, six or seven residues. A series of peptides were synthesized for these studies whose sequences are depicted in Table 1.

TABLE 1

| | ($NH_2 \rightarrow COOH$) | |
|---|---|---|
| Acronym | Sequence | SEQ ID NO: |
| KK1-1 | Val-Gln | |
| KK1-2 | Ser-Val-Gln | |
| KK1-3 | Arg-Ser-Val-Gln | 1 |
| KK1-4 | Phe-Arg-Ser-Val-Gln | 2 |
| KK1-5 | Pro-Phe-Arg-Ser-Val-Gln | 3 |
| KK1-6 | Ser-Pro-Phe-Arg-Ser-Val-Gln | 4 |
| KK1-7 | Cha-Phe-Arg-Ser-Val-Gln | 5 |
| KK1-8 | Ada-Phe-Arg-Ser-Val-Gln | 6 |
| KK1-9 | Pro-Phe-Arg-Ser-Val | 7 |
| KK1-10 | Pro-Phe-Arg-Ser-Val-Gln-Val | 8 |
| KK1-11 | Leu-Met-Lys-Arg-Pro-Pro | 9 |
| KK1-12 | Arg-Pro | |
| KK1-13 | Lys-Arg-Pro | |
| KK1-14 | Met-Lys-Arg-Pro | 10 |
| KK1-15 | Leu-Met-Lys-Arg-Pro | 11 |
| KK1-16 | Ser-Leu-Met-Lys-Arg-Pro | 12 |
| KK1-17 | Chg-Phe-Arg-Ser-Val-Gln | 13 |
| KK1-18 | Chg-Phe-Arg-Ser-Val-Gln | 14 |
| KK1-19 | Pro-Phe-Arg-Ser | 15 |
| KK1-20 | Pro-Phe-Arg | |
| KK1-21 | Pro-Phe | |
| KK1-22 | Phe-Arg | |
| KK1-23 | Phe-Arg-Ser | |
| KK1-24 | Ser-Pro-Phe-Arg | 16 |
| KK1-25 | Ser-Pro-Phe-Arg-Ser | 17 |
| KK1-26 | Arg-Ser | |
| KK1-27 | Pro-Phe-Arg-Ser-Ser-Arg | 18 |
| KK1-28 | Pro-Phe-Arg-Ser-Val-Arg | 19 |
| KK1-29 | Thr-Ser-Leu-Met-Lys-Arg-Pro | 20 |
| KK1-30 | Thr-Ser-Leu-Met-Lys-Arg-Pro-Pro | 21 |
| KK1-31 | Leu-Met-Lys-Arg | 22 |
| KK1-32 | Leu-Met-Lys | |
| KK1-33 | Leu-Met | |
| KK1-34 | Gly-Pro-Aab-Lys-Ala-Arg-Ile-Ile | 23 |
| KK1-35 | Gly-Pro-Aab-Lys-Ala-Arg-Ile | 24 |
| KK1-36 | Gly-Pro-Aab-Lys-Ala-Arg | 25 |
| KK1-37 | Gly-Pro-Aab-Lys-Ala | 26 |
| KK1-38 | Gly-Pro-Aab-Lys | 27 |
| KK1-39 | Gly-Pro-Aab | |
| KK1-40 | Gly-Pro | |
| KK1-41 | Val-Tyr-Gly-Cys(Acm)-Arg | 28 |
| KK1-42 | Tyr-Gly-Cys(Acm)-Arg | 29 |
| KK1-43 | Gly-Gly-Cys(Acm)-Arg | 30 |
| KK1-44 | Gly-Cys(Acm)-Arg | 31 |
| KK1-45 | Cys(Acm)-Arg | |
| KK1-46 | Gly-Cys-Arg-Pro-Cys-Lys | 32 |
| KK1-47 | Gly-Cys-Arg-Gly-Pro-Cys-Lys | 33 |
| KK1-48 | Gly-Cys-Arg-Gly-Gly-Pro-Cys-Lys | 34 |
| KK1-49 | | |
| KK1-50 | Phe(4-Am)-Ser-Val-Gln | 35 |

TABLE 1-continued (NH$_2$ → COOH)

| Acronym | Sequence | SEQ ID NO: |
|---|---|---|
| KKl-51 | Pro-Phe-Phe(4-Am)-OBzl | 36 |
| KKl-52 | Pro-Phe-Phe(4-Am)-OGlc-Val-Gln | 37 |
| KKl-53 | Gly-Pro-Aab-Phe(4-Am)-Ala-Arg-Ile-Ile | 38 |
| KKl-54 | Ser-Val-Glu-Val | 39 |
| KKl-55 | Pro-Phe-boroArg | |
| KKl-56 | Pro-Phe-Arg-CH$_2$F | 40 |
| KKl-57 | Pro-Phe-Arg | |
| KKl-58 | Leu-Val-Arg | |
| KKl-59 | Pro-Phe-Arg-Leu-Val-Arg | 41 |
| KKl-60 | Gly-Pro-Aab-Arg-Ala-Arg-Ile-Ile | 42 |
| KKl-61 | Gly-Pro-Phe-Arg-Ala-Arg-Ile-Ile | 43 |
| KKl-62 | Gly-Pro-Aab-Arg-Ser-Arg-Ile-Ile | 44 |
| KKl-63 | Gly-Pro-Aab-Lys-Ala-Val-Ile-Ile | 45 |
| KKl-64 | Ser-Pro-Phe-Arg-Ser-Val-Glu-Val | 46 |
| KKl-65 | Ser-Val | |
| KKl-66 | Ser-Pro-Phe-Arg-Ser-Val | 47 |
| KKl-67 | Phe-Arg-Val-Glu-Val | 48 |
| KKl-68 | Phe-Arg-Ser-Val-Glu-Val | 123 |
| KKl-69 | Phe-Arg-Ser-Val | 49 |
| KKl-70 | Arg-Ser-Val | |
| KKl-71 | Ser-Pro-Phe | |
| KKl-72 | Ser-Pro | |
| KKl-73 | Ala-Arg-Ile-Ile | 50 |
| KKl-74 | Ile-Ile | |
| KKl-75 | Arg-Ile-Ile | |
| KKl-76 | Thr-Gly-Pro-Aab-Lys-Ala-Arg-Ile-Ile | 51 |
| KKl-77 | Aab-Lys-Ala-Arg-Ile-Ile | 52 |
| KKl-78 | Lys-Ala-Arg-Ile-Ile | 53 |
| KKl-80 | Gly-Phe-Arg-Ser-Val-Gln | 54 |
| KKl-81 | [D-Ala]-Phe-Arg-Ser-Val-Gln | 55 |
| KKl-82 | [D-Aab]-Phe-Arg-Ser-Val-Gln | 56 |
| KKl-83 | [D-Val]-Phe-Arg-Ser-Val-Gln | 57 |
| KKl-84 | [D-t-BuGly]-Phe-Arg-Ser-Val-Gln | 58 |
| KKl-85 | [D-Ile]-Phe-Arg-Ser-Val-Gln | 59 |
| KKl-86 | [D-Chg]-Phe-Arg-Ser-Val-Gln | 60 |
| KKl-87 | [D-Ile(4Me)]-Phe-Arg-Ser-Val-Gln | 61 |
| KKl-88 | [D-Adg]-Phe-Arg-Ser-Val-Gln | 62 |
| KKl-89 | Ser-Val-Gln | |
| KKL-90 | Pro-Phe-Arg-Ser-Val-Gln | 3 |
| KKl-91 | Pro-Phe(4NH$_2$)-Arg-Ser-Val-Gln | 63 |
| KKL-92 | Pro-Phe(4-OH)-Arg-Ser-Val-Gln | 64 |
| KKl-93 | Pro-Phe(4-CN)-Arg-Ser-Val-Gln | 65 |
| KKl-94 | Pro-Phe(4-NO$_2$)-Arg-Ser-Val-Gla | 66 |
| KKl-95 | Pro-Phe(4-OCH$_3$)-Arg-Ser-Val-Gln | 67 |
| KKl-96 | Pro-Phe(4-OC$_6$H$_5$)-Arg-Ser-Val-Gln | 68 |
| KKl-97 | Pro-Phe(4-I)-Arg-Ser-Val-Gln | 69 |
| KKl-98 | Pro-Phe(4-Br)-Arg-Ser-Val-Gln | 70 |
| KKl-99 | Pro-Phe(4-Cl)-Arg-Ser-Val-Gln | 71 |
| KKl-100 | Pro-Phe(4-F)-Arg-Ser-Val-Gln | 72 |
| KKl-101 | Pro-Phe(4-CH$_3$)-Arg-Ser-Val-Gln | 73 |
| KKl-102 | Pro-Phe(4-COCH$_3$)-Arg-Ser-Val-Gln | 74 |
| KKl-103 | Pro-Phe(4-NHCOCH$_3$)-Arg-Ser-Val-Gln | 75 |
| KKl-104 | Prn-Phe(4-CH$_2$OH)-Arg-Ser-Val-Gln | 76 |

Figure 2B:
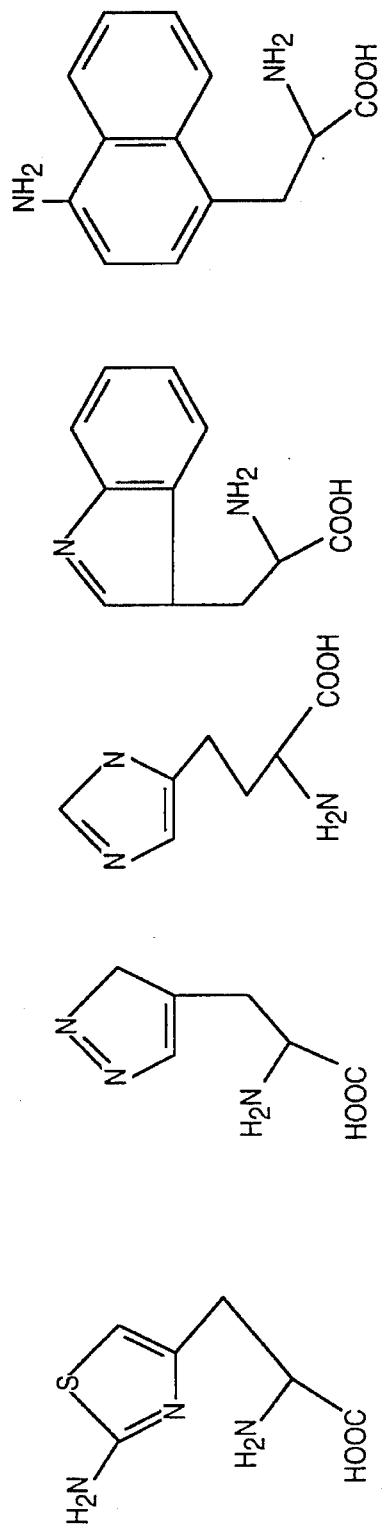

The sequence of the peptides of the invention comprise a series of naturally or non-naturally occurring amino acids or modified amino acids, or amino acid derivatives, wherein the sequence comprises at least a portion which is analogous to the sequence of human and bovine tissue kallikrein from positions 388 to 390 wherein the portion of the peptide corresponding to position 389 is 4-aminophenylalanine (Phe(4NH$_2$) or Aph) or a similar residue. A similar residue is a chemical structure which is structurally and/or functionally comparable to Phe(4NH$_2$). Such structures may be naturally or non-naturally occurring (non-coding) amino acids, modified amino acids, or derivatives of amino acids. Such structures can be identified by applying the techniques of rational drug design, wherein emphasis is placed on whether a ligand fits into a binding site using molecular modeling in view of the energetics of the reaction between the binding site and the substrate. The blend of geometric and algebraic approaches allows the quantitative assessment of proposed interactions. Some amino acid structures which are similar to Phe(4NH$_2$) are depicted in FIG. 2. Hydrogen bonding, ionic interactions, van der Waals' forces, and a chemical's interaction with water molecules are all important in determining a correct fit. Preferably the peptide sequence corresponds to at least positions 388 to 390 of human tissue kallikrein and contains a Phe(4NH$_2$) residue, and more preferably the peptide has the sequence (SEQ. ID. NO. 128): Pro-Phe-Phe(4NH$_2$)-Ser-Val-Gln-NH$_2$.

The peptides of the invention are substrate analogs that specifically inhibit the androgen, tissue kallikrein. The K$_I$ for the substrate analogs of the invention is less than 50 μm, preferably about 21 μm, more preferably less than 1.0 μm, and still more preferably less than 0.1 μm. Surprisingly the peptides do substantially inhibit the activity of plasma kallikrein or other enzymes typical to plasma such as trypsin, human thrombin, plasmin, urokinase, trypsin, and the enzymes of the clotting and complement cascades. The addition of the Phe(4NH$_2$) residue to the peptide in a factor is conferring the peptide's specificity for tissue kallikrein. The Phe(4NH$_2$) residue is also a factor in reducing the peptide's overall ionic character, or charge, with respect to the corresponding sequence of tissue kallikrein. The relatively neutral Phe(4NH$_2$) corresponds to the highly charged arginine residue at position 389. This charge reduction of the overall peptide does not reduce the ability of the peptide to bind to and inhibit the activity of tissue kallikrein and makes it possible for the peptide to be absorbed through a biological membrane such as the epithelium of the gastrointestinal tract. If necessary, other amino acids and other chemical residues may also be altered to further reduce the overall charge of the peptide.

Another embodiment of the invention is directed to compositions containing substrate analogs useful for the prevention or treatment of physiological effects caused by or related to tissue kallikrein activity. These compositions comprise the above-described peptides and, preferably, contain a physiologically acceptable carrier. Examples of suitable physiological carriers can be found in *Remington's Pharmaceutical Sciences*, 18th Edition (A. Gennaro, editor, Mack Pub., Easton, Pa. 1990), which is hereby specifically incorporated by reference. Preferable examples of physiologically acceptable carriers are water, oil, alcohol, saline, glycerol, polysaccharide, starch, and combinations thereof. Compositions of the invention may also include stabilizers and flavor enhancing substances to increase composition shelf life, if necessary, and palatability.

Still another embodiment of the invention is directed to methods for the prevention or treatment of biological or physiological affects which can be attributed, at least in part, to the activity of tissue kallikrein. Compositions containing therapeutically or prophylactically effective amounts of substrate analogs of tissue kallikrein comprising the above-described peptides and can be administered to a patient which is preferably a human. Effective amounts of a composition are those amounts which are necessary to alleviate conditions or symptoms produced by the disease or disorder. Compositions of the invention may be administered to a patient orally, parenterally, sublingually, rectally, enterally, by pulmonary absorption, or by topical application. Parenteral injections may be intraperitoneal, intravenous, subcutaneous, intramuscular, intrathecal, intra-arterially, or by a medi-port system. Preferably the administration is oral.

Methods of the invention are directed to the treatment or prevention of disorders and symptoms associated with tissue kallikrein activity. These compositions may be administered to a patient, preferably a human, who is suffering from a condition which would be alleviated by the inhibition of tissue kallikrein activity. Tissue kallikrein, among other activities, cleaves inactive kallidine, or kininogen, into its activated form, kinin or bradykinin. Specific receptors recognize and bind to each type or set of kinins and produce a specific physiological effect. For example, bradykinin, also called kallidin I, is a potent stimulator of vasodilation. It stimulates visceral smooth muscle and relaxes vascular smooth muscle. Inhibition of the production of bradykinin results in a vasoconstriction and a comparable increase of blood pressure locally and/or systemically.

Bradykinin is also one of the physiological mediators of anaphylaxis. It is released from cytotoxic antibody-coated mast cells following reaction with an antigen specific for the antibody. Compositions of specific kallikrein inhibitors would be useful to alleviate conditions associated with rhinitis, such as vascular permeability of the sinuses. Compositions could be administered systemically such as by oral formulation, or locally such as by spraying directly into the sinuses.

Kinins regulate such conditions as blood pressure, edema, vascular leakage, and blood flow to and around certain organs of a body. A composition administered to a patient suffering from hypotension, or decreased blood pressure, would inhibit kallikrein activity, thereby reducing kinin levels. Kinins function to increase vascular permeability which lowers blood pressure. Thus, their absence would raise blood pressure. Individuals with lowered blood pressure or hypotension, either periodically or for long periods of time could be administered compositions containing kallikrein inhibitors which would quickly and safely raise blood pressure. Treatment can be localized to a specific organ, tissue or area of the body or could be systemic to raise the body's overall blood pressure. Treatments could be sustained for patients with chronic hypotension or periodic for patients who are hypotensive for short periods of time such as, for example, while under medication, in surgery, suffering from physical trauma such as trauma which causes internal or external blood loss, or where an immediate response is desired. Inflammation due to rheumatoid arthritis, allergic reactions, and other disorders of the immunological system may be treatable or preventable with compositions of the invention.

Kinins are also involved in synthesis and release of several inflammatory mediators including prostaglandins, leukotrienes and thromboxanes through the arachidonic acid pathway. Cells that may be involved are neutrophils, macrophages, lymphocytes; mast cells, and other lamina propria cells, including fibroblasts. Compositions containing specific inhibitors of tissue kallikrein may be administered to a patient, which is preferably a human, to decrease an inflammation. The inflammatory reaction may be local, as occurs with localized infections, cuts and abrasions, or surgical procedures. Compositions could be administered as a swab or wash, a transdermal patch, or by injection. Alternatively, inflammation may be systemic as seen with certain bacterial infections such as sepsis due to gram negative or positive microorganisms, certain virus such as influenza and parainfluenza, herpes simplex, varicella-zoster, corona, respiratory syncytial, cytomegalovirus, rhinovirus, and hepatitis, and certain fungi and yeast such as sarcoidosis.

Specific tissue kallikrein inhibitors effect the processing and/or expression of many different cytokines such as tumor necrosis factor, epidermal growth factor-binding protein (EGF-BP), nerve growth factor (NGF), bovine adrenal medula neuropeptide (BAM) 22P, atriopeptigen, insulin, renin, tissue plasminogen activator, atrial naturietic factor, low density lipoprotein, and other enzymes such as collagenase. When control of cytokine level is desired, the substrate analogs of the invention may be administered to decrease, or increase if necessary, the processing of these cytokines and their subsequent effect.

Kinins are also involved in the perception of pain. Compositions of the invention can be administered to a patient, preferably a human, to alleviate or prevent pain. The perception of pain may be due to a physical trauma to the body such as a chemical, thermal or mechanical injury. Compositions of the invention may be suitable as substitutes or adjuvants for anesthetic such as prior to or during a painful medical procedure. Compositions may be applied either locally or systemically, as necessary, to interfere with tissue kallikrein activity and block the patient's perception of pain. This would be useful in many application such as, for example, out-patient procedures where the lingering effects of conventional anesthetics require an extended hospital stay or restricted activity. Specific inhibitors of tissue kallikrein have no such drawbacks. There are no secondary effects such as drowsiness or disorientation because the mechanism of action does not involve suppression of neuronal activity. Examples of circumstances where specific kallikrein would be useful include minor surgeries such as, for example, dental surgery, biopsies, and exploratory procedures.

Treatments with kallikrein inhibitors would also be useful to treat localized infections, which may be internal or external, to speed recovery. For example, external infection such as fungal infections are quite irritating and spread rapidly. Avoidance of all contact with the infected area is usually preferred to prevent or reduce inflammation of the afflicted area. This is usually difficult due to the intense irritation of inflammation which is often manifested as itching. Compositions of the invention, administered externally or internally directly to the affected area, and possibly systemically, decrease the inflammation and the perception of irritation allowing the patient to recover with a minimum of discomfort.

The following examples are offered to illustrate embodiments of the invention, but should not be viewed as limiting the scope of the invention.

EXAMPLES

Example 1

Purification of Kallikrein

Human urinary kallikrein (HUK) was purified from human urine. Briefly, urine was subjected to ultrafiltration to concentrate the protein components which were applied to approtinin-CH-Sepharose affinity columns. Active fractions from these columns were next applied to Sephadex G-100 gel filtration and collected as fractions. The pH of each fraction was determined immediately upon elution, and the fraction was neutralized by addition of 2.0 ml of 2M Tris-HCL buffer, pH 8.0. Porcine pancreatic 24-kallikrein (PPK), at 50 units/mg protein; 1.0 units hydrolyses 1.0 µM BAEE (benzoyl -L-arginine ethyl ester) to N-ā-benzoyl-L-arginine/minute at pH 8.7 at 25° C., was purchased from Sigma Chemical Company (St. Louis, Mo.). The rate of hydrolysis of BAEE was unaffected in the presence of lima bean trypsin inhibitor, indicating that the enzyme preparations contained little, if any, active trypsin. All other enzymes were purchased from Sigma Chemical Company (St. Louis, Mo.).

Example 2

Synthesis of Peptides

Peptides were prepared by solid phase techniques essentially as described by R. B. Merrifield (J. Amer. Chem. Soc. 85:2149–54, 1963). tert-butyloxycarbonyl amino acids were purchased from Peninsula Laboratories (San Mateo, Calif.). Support for the solid-phase synthesis was p-methylbenzylhydrylamine resin containing 0.47 micromoles of $NH_2/g$ (United States Biochemical; Cleveland, Ohio). Dioxane (Fisher; Medford, Mass.) was redistilled from sodium. Six normal HCl-dioxane was prepared. by bubbling electronic-grade HCl gas (Matheson, Gloucester, Mass.) through dioxane cooled in an ice bath. The concentrated solution was then diluted to 6N and stored in a closed container. Other reagents were of particle grade.

Synthetic reactions were performed in 60 ml polypropylene syringes fitted with a frit (70 μm porosity, Bolab, Derry, N.H.) by using apparatus and techniques as described by J. Burton et al. (Biochem. 14:3892–98, 1975). Completeness of coupling was judged by the ninhydrin test both by observing the bulk reaction and by viewing the beads on filter paper at 40× under a dissecting microscope. Some of the peptides formed are depicted in Tables 1–7. Peptide analysis was performed by hydrolysis at 105° C. for 24 hours under vacuum in 6N HCl. Amino acid analyses were performed with a Beckman D-6000 analyzer. UV spectra were obtained on an HP8590A spectrophotometer equipped with an HP7445A plotter (Hewlett-Packard; Palo Alto, Calif.). HPLC purifications were done on a Beckman octadecylsilane (ODS) column (1×25 cm) with a gradient of 0–100% $CH_3CN$-0.2%, $CF_3COOH$ in $H_2O$-0.2% $CF_3COOH$ over 20 minutes.

Using rational drug design, amino acid structures which may be useful as substitutions of the Arg residue at position 389 of the kininogen platform sequence (positions 386–392) in substrate analogs were conceived and some tested for specific inhibition of tissue kallikrein (FIG. 2). Emphasis was placed on whether the ligand fits into a binding site (molecular modeling), and also on the energetics of the process using mathematical (geometric and algebraic) techniques to calculate the binding energies associated with various interactions.

Example 3

Inhibition/Binding Assays

The determination of Michaelis constant ($K_M$), inhibitor constant ($K_I$), and the maximum velocity of hydrolysis ($V_{max}$) of individual substrate analogue inhibitors was performed. $K_M$ determination was made by hydrolysis of the substrate analogue inhibitors by HUK. The test inhibitor was combined at different concentrations on either side of the $K_M$ value with the enzyme of pH 9.0 for thirty minutes at 37° C. The cleavage products were separated from the starting material in the digest by HPLC on a Beckman ODS column (1×25 cm) using a thirty minute gradient of from 0–70% $CH_3CN$ in triethylammonium phosphate buffer, pH 7.0. The starting materials and reaction products were completely resolved under these conditions. Absorbance of the HPLC effluent was monitored at 220 nm. Individual fractions were collected and the amount of peptide degradation products was quantitated by counting in a liquid scintillation counter. Samples containing individual inhibitors were incubated without HUK and solvent blanks were also chromatographed and analyzed in the same way. Control runs in which the entire HPLC effluent was collected as a series of 10 fractions demonstrated that greater than 95% of the applied radioactivity was recovered and the expected products of kallikrein cleavage were not further degraded into smaller peptides.

For test purposes, individual peptide sequences were synthesized, purified, and characterized as described herein. For these cleavage studies, doubly labelled peptides were prepared using [$^3$H]-valine and [$^3$H]-proline respectively. In addition, 6.0N HCL-dioxane was used for removal of tert-butoxycarbonyl protecting groups and 90% hydrogen fluoride/10% anisole (volume/volume) for global deprotection on completion of the synthesis. After extraction and gel filtration on Sephadex G-15, final purification was completed by isocratic elution from a synchrom RP-HPLC column (2.1×25 cm) with $CH_3CN$-$H_2O$ (8 ml/min). The resultant peptides were deemed to be homogeneous by amino acid analysis, HPLC, TLC, and $A_{230}/A_{260}$ ratio analysis.

$K_I$ measurements were performed using a HP8450A diode array spectrophotometer (Hewlett Packard; Palo Alto, Calif.) attached to a Model 216 computer using the multi-component assay program modified to allow simultaneous determination of reaction velocity in four samples. Dixon plots were used for data reduction and for calculation of $V_{max}$. The substrate analogues were examined for inhibition of the capacity of HUK to cleave p-nitroaniline (pNA) from the chromogenic substrate S-2266 (D-Val-Phe-Arg-pNA) (Kabi; Stockholm, Sweden) at pH 9.0 and 37° C.

Inhibition of biologically active kinin from low molecular weight kininogen was done at pH 7.7 and 37° C. The $K_I$ values for the preliminary analog inhibitors reported previously by H. Okunishi et al. (Hypertension 7:172–75, 1985). These inhibitors were rapidly cleaved by HUK. A quantitative assessment of the capacity of these specific analogue inhibitors is shown by the $K_M$ the turnover number, and the relative specificity for each of these previously reported substrate analogues.

Example 4

Inhibition Assays using Substrate Analogs with $P_3$ Substitutions

The $P_3$ subsite, into which the proline fits, was the first position to be examined systematically. Data shown in FIG. 1 indicate that it is not particularly important for binding to tissue kallikrein. Less than 3% of the total binding energy of the substrate analogues can be ascribed to this residue.

FIG. 3 shows the amino acid analogues prepared to examine the relationship between the physical properties of the inhibitor and $K_I$ at $P_3$. Listed in Table 2 are $K_I$ values along with changes in volume (ΔV), measured lipophilicity ($\Delta K_{O/W}$), and calculated lipophilicity (ΔCLOGP). Some of the substrates containing a D-amino acid residue at $P_3$ are rapidly hydrolyzed by tissue kallikrein. To overcome this problem, a new method was also used to determine $K_I$ (see Example 6).

TABLE 2

| KKIN[2] | Residue | $K_I$ (mM) | log $K_I$ | ΔLog $K_{O/W}$ | ΔCLOGP | ΔV $A^3$ | SEQ. ID NO. |
|---|---|---|---|---|---|---|---|
| 80 | Gly | 80 | 4.10 | 0.00 | 0.00 | 0 | 54 |
| 81 | D-Ala | 50 | 4.30 | 0.04 | 0.31 | 14 | 55 |
| 82 | D-Abu | 44 | 4.36 | 0.01 | 0.83 | 28 | 56 |
| 83 | D-Val | 101 | 4.00 | 0.10 | 1.23 | 42 | 57 |
| 84 | D-t-BuGly | 75 | 4.12 | 0.86 | 1.63 | 56 | 58 |
| 85 | D-Ile | 34 | 4.47 | 0.33 | 1.77 | 56 | 59 |
| 86 | D-Chg | 84 | 4.08 | 0.58 | 2.42 | 82 | 60 |
| 87 | D-Ile(4Me) | 141 | 3.85 | 1.11 | 2.30 | 70 | 61 |
| 88 | D-Adg | 50 | 4.30 | 1.88 | 3.43 | 134 | 62 |
| 90 | Pro | 101 | 4.00 | 0.16 | 3.20 | 63 | 3 |
| 105 | D-aIle | 57 | 4.24 | 0.15 | 2.21 | 56 | 77 |

There is no statistically significant relationship between $K_I$ and any single variable listed in Table 2 ($r^2 < 0.03$). As a result there is no obvious series of modifications at $P_3$ which can be used to improve $K_I$. The best inhibitor, KKI-85 ([D-Ile]hexapeptide, 34 μM), binds to β-PPK about 3-fold better than the platform peptide KKI-90 which has a prolyl residue at $P_3$ (101 μM). The difference in binding energy between the two substitutions (ΔΔG) is −666 cal mol⁻[−6336−(−5670)]. ΔΔG for the $P_3$ subsite is 181 cal mol⁻. The D-Ile substitution allows ΔΔG for each residue to increase by 3.5-fold(−666/−181) and still maintain the specific binding profile shown in FIG. 1. If substitutions which allow the maximum increase in free energy of binding can be found for all residues, the platform hexapeptide would have a ΔΔG of −18,305 cal mol⁻¹ {3.5×[(−181)+(−847)+(−2114)+(−1436)]} ($K_I$, 0.12 pM). Alternatively, if a tetrapeptide having the inhibitory profile shown in FIG. 1 and a $K_I$ value of 1 nM (12,700 cal mol⁻¹) was desired, the value of ΔΔG for each residue would need to. be increased 2.8-fold.

Example 5

Inhibition Assays Using Substrate Analogs with $P_2$ Substitutions

FIG. 1 shows that the $P_2$ subsite contributes significantly to total binding energy of tissue kallikrein. The strategy employed to determine useful modifications for the $P_2$ residue is, first, to identify the type of interaction which is responsible for binding and then to enhance this property.

Interactions between drugs and their receptors include: lipophilicity ($K_{O/W}$), polarizability (CMR), hydrogen bond donor and acceptor ability ($H_A$, $H_D$), inductive (I) and resonance effects (R). Physical models of what these parameters describe are given in *Substiutent Constants for Correlation Analysis in Chemistry and Biology* (C. Hansch and A. Leo editors, John Wiley & Sons, New York, 1979).

A major problem in assigning a particular type of interaction to a given amino acid residue is that any replacement can change several parameters at the same time. Substitutions which increase lipophilicity at $P_2$, usually increase polarizability as well. The co-relatedness of parameters prevents any alterations in $K_I$ from being clearly assigned to a single property that may be subsequently manipulated to increase affinity.

TABLE 3

Congener breaking set used to determine the type o binding interaction at P2

| Substitution | CLOGP* | CMR* | $H_A$ | $H_D$ | F | R | SEQ. ID NO. |
|---|---|---|---|---|---|---|---|
| —H | 0.17 | 5.82 | 0 | 0 | 0.00 | 0.00 | 3 |
| —NH2 | −1.34 | 6.19 | 1 | 1 | 0.02 | −0.68 | 63 |
| —OH | −0.78 | 5.97 | 1 | 1 | 0.29 | −0.64 | 64 |
| —CN | −0.68 | 6.29 | 1 | 0 | 0.51 | 0.19 | 65 |
| —NO₂ | −0.37 | 6.54 | 1 | 0 | 0.67 | 0.16 | 66 |
| —OCH₃ | −0.20 | 6.43 | 1 | 0 | 0.26 | −0.51 | 67 |
| —OCH₅ | 1.98 | 8.48 | 1 | 0 | 0.34 | −0.35 | 68 |
| —I | 1.00 | 7.12 | 0 | 0 | 0.40 | −0.19 | 69 |
| —Br | 0.75 | 6.59 | 0 | 0 | 0.44 | −0.17 | 70 |
| —Cl | 0.60 | 6.31 | 0 | 0 | 0.41 | −0.15 | 71 |
| —F | 0.03 | 5.83 | 0 | 0 | 0.43 | −0.34 | 72 |
| —CH₃ | 0.53 | 6.28 | 0 | 0 | −0.04 | −0.13 | 73 |
| —COCH₃ | −0.68 | 6.78 | 1 | 0 | 0.32 | 0.20 | 74 |
| —NHCOCH₃ | −1.10 | 7.15 | 1 | 1 | 0.28 | −0.26 | 75 |
| —CH₂OH | −1.15 | 6.43 | 1 | 1 | 0.00 | 0.00 | 76 |

*MedChem 3.533

It is possible to design a series of substitutions in which the various in interactions are not strongly co-related. These are called congener breaking series. Table 3 lists a congener breaking series of analogues which should identify the type of interactions at the $P_2$ subsite. Twelve of the 15 amino acids in this series have been prepared and incorporated into analogs of the platform sequence (SEQ. ID. NO. 3): Pro-Phe-Arg-Ser-Val-Gln.

Boc-Phe(4CH₂OH), and Boc-Phe(For) have been prepared by Friedel-Crafts acylation of N-phthaloyl protected phenylalanine. This reaction has not been previously reported for phenylalanine and may simplify the synthesis of other analogues of this amino acid.

Example 6

Inhibition Studies Using Substrate Analogs $K_I$ determination were made using the Biomek 1000 system (Beckman; Foster city, Calif.). This method estimates the $K_I$ of three inhibitors simultaneously, testing each over a 3000-fold range of concentrations. The results from the screening test are employed to adjust the concentration of inhibitors used so that an optimal determination of the $K_I$ value can be made. In this method, a peptide substrate was cleaved by a protease to release a free alpha-amino group. This was quantitated by reaction with trinitrobenzene sulfonic acid. Measurement of the velocity of cleavage as a function of the substrate concentration then yields $K_M$ values for the cleavage reaction. A decrease in cleavage rate when inhibitors were added then yielded $K_I$ values using the standard Dixon approach. This method allowed for the assay of proteases for which no convenient chromogenic substrate exists. The much larger molar extinction coefficient (90,000 v. 15,000) made these assays substantially more sensitive than those which involve cleavage of p-nitroanilide substrates.

Assay methods were based on the cleavage of chromogenic substrate S-2266 (D-Val-Leu-Arg-pNA) (Kabi; Charlotte, N.C.) by porcine pancreatic kallikrein (Sigma Chemical Company; St. Louis, Mo.) to yield an increase in absorbance at 405 nm. By changing the substrate and enzyme, the general method has been extended to measure the inhibition of human tissue kallikrein (HTK or human urinary kallikrein HUK), human plasma kallikrein (HPK), plasmin, and urokinase (UK). In all assays, the robot dilutes the inhibitor into a series of wells and adds substrate and buffer. Chromogenic reactions are started by the addition of enzyme. Changes in the absorbance at 405 nm in an array of wells were recorded. All manipulations were performed by the instrument from reservoirs containing substrate, inhibitor, diluent (water), buffer, or enzyme.

Results of inhibition studies using substrate analogs of kininogen are shown in Tables 4, 5, 6 and 7. Most substrate analogs with $P_2$ substitutions had comparable $K_I$ values when tested against PPK, HUK and HPK (Table 4). $P_2$ substitutions of oFPhe, Thi, 2Nal, 1Nal, mTyr, mFPhe and Cha demonstrated some specificity for tissue kallikrein over plasma kallikrein. $P_1$ substitutions of Arg, Gln and SeCys2 showed a, respectively, 15-fold, 6-fold and an 89-fold selectivity for porcine pancreatic kallikrein over plasma kallikrein (Table 5). The substrate analogs depicted in Table 6 demonstrated inhibition of HPK, consequently most were not tested against HUK or PPK. However, KIDZ-2, -6, and -15 demonstrated selectivity for tissue kallikrein over plasma kallikrein or urokinase (Table 7). KIDZ-6 showed the best specificity for tissue kallikrein in this experiment. Both PPK and HUK $K_I$ values were under 50 where as the $K_I$ values against HPK and UK were nearly 500-fold greater.

TABLE 4

Platform Sequence = Pro-X-Arg-Ser-Val-Gln

| X | Acronym | $K_I$ (micromoles) PPK | HUK | HPK | SEQ. ID. NO. |
|---|---|---|---|---|---|
| Phe | KKI-90 | 117(48) | 103 (112) | (159) | 3 |
| oFPhe | KCH-1 | 124 | 151 | 472 | 78 |
| hPhe | KCH-2 | 402 | — | 545 | 79 |
| Pal | KCH-3 | 381 | — | — | 80 |
| Thi | KCH-4 | 109 | 249 | 497 | 81 |
| Phg | KCH-5 | 1323 | — | ni | 82 |
| 2Nal | KCH-6 | 133 | 114 | 665 | 83 |
| 1Nal | KCH-7 | 130 | 41 | 516 | 84 |
| mTyr | KCH-8 | 184 | — | 401 | 85 |
| mFPhe | KCH-9 | 158 | 73 | 443 | 86 |
| Cha | KCH-10 | 85 | 92 | 813 | 87 |
| Trp | KCH-11 | 230 | — | 449 | 88 |
| Trp(CHO) | KCH-12 | 300 | — | — | 89 |
| MeNal | KCH-13 | — | — | — | 90 |
| Anth | KCH-14 | — | — | — | 91 |

TABLE 5

Platform Sequence = Pro-Phe-Arg-X-Val-Gln

| X | $K_I$ (micromoles) PPK | HUK | HPK | SEQ. ID. NO. |
|---|---|---|---|---|
| Ser | 117(48) | 103(112) | (159) | 3 |
| Asn | 58, [33], 99, 67 | 99 | 244 | 92 |
| Asp | 450 | | | 93 |
| Arg | (15–19) | | 236 | 94 |
| Cys | 58 | | | 95 |
| Cys2 | 16, 27, [65] | | | 96 |
| Gln | 188, 230 | | 1396 | 97 |
| Hse | 163 | | 359 | 98 |
| Secys2 | 24, 29, 46 | | 1171 | 99 |
| D-Ser | 1116 | 100 | | 100 |
| Ala | 131, 161 | | 536 | 101 |
| Thr | 216 | | | 102 |
| F3-Thr | | | | 103 |
| OH-Asn | | | | 104 |

[ ]Dithiothreitol

TABLE 6

| Analog | $K_I$ (micromoles) PPK | HUK | HUK | SEQ. ID. |
|---|---|---|---|---|
| Pro-Phe-Arg-Ser-Val-Gln | 117,65 (48) | 103 | (159 | 3 |
| Pro-Phe-Arg-Ser-Ser-Arg | 60 | 54 | 490 | 105 |
| Val-Phe-Arg-Asn-Ser-Arg | | | 194 | 106 |
| Val-Phe-Arg-Asn-Asn-Arg | | | 124 | 107 |
| Pro-Phe-Arg-Ser-Arg-Gln | | | | 108 |
| Pro-Phe-Arg-Asn-Arg-Gln | | | | 109 |
| Pro-Arg-Arg-Ser-Val-Gln | | | | 110 |
| ChCar-Phe-Arg-dia-Val-Gln | 114 | | 985 | 111 |
| Arg-Phe-Arg-Asn-Arg-Gln | | | 52 | 112 |
| Phe-Phe-Arg-Asn-Arg-Gln | | | 151 | 113 |
| Phe-Phe-Arg-Asn-Arg-Gln | | | 1528 | 114 |
| Val-phe-Arg-Ser-Arg-Gln | | | | 115 |
| Val-Phe-Arg-Asn-Arg-Gln | | | 532 | 116 |
| Val-Phe-Arg-Asn-dArg-Gln | | | 1568 | 117 |
| Val-Phe-Arg-Asn-Lys-Gln | | | | 118 |
| Val-phe-Arg-Asn-hArg-Gln | | | 371 | 119 |
| Val-Phe-hArg-Asn-Aph-Gln | | | | 120 |
| Val-Phe-hArg-Asn-hArg-Gln | 2.9;10 | | 298 | 121 |
| Pro-Cys-Lys-Ala-Arg-Ile | 0.003 | | 0.18 | 122 |

TABLE 7

| Analog (NH$_2$→COOH) | Acronym | K$_i$(micromoles) | | | | SEQ. ID. NO. |
|---|---|---|---|---|---|---|
| | | PPK | HUK | HPK | UK | |
| Pro-Phe-Arg-Ser-Val-Gln | KIDZ-1 | 23 | — | 116 | >20 mM | 3 |
| Pro-Phe-Lys-Ser-Val-Gln | KIDZ-2 | 294 | — | 2500 | >20 mM | 124 |
| Pro-Phe-Orn-Ser-Val-Gln | KIDZ-3 | >5 mM | — | >5 mM | >20 mM | 125 |
| Pro-Phe-Kbu-Ser-Val-Gln | KIDZ-4 | >5 mM | — | >5 mM | — | 126 |
| Pro-Phe-Kpr-Ser-Val-Gla | KIDZ-5 | >5 mM | — | >5 mM | — | 127 |
| Pro-Phe-Aph-Ser-Val-Gla | KIDZ-6 | 36 | 21 | >10 mM | >20 mM | 128 |
| Pro-Phe-Cit-Ser-Val-Gln | KIDZ-7 | >3 mM | — | >5 mM | — | 129 |
| Pro-Phe-hLys-Ser-Val-Gln | KIDZ-8 | 203 | — | — | 130 | |
| Pro-Phe-hAph-Ser-Val-Gln | KIDZ-9 | >1 mM | — | 5 mM | >20 mM | 131 |
| Pro-Phe-Pal-Ser-Val-Gln | KIDZ-10 | >1 mM | — | >20 mM | >20 mM | 132 |
| Pro-Phe-hCit-Ser-Val-Gln | KIDZ-11 | — | 133 | | | |
| Pro-Phe-His-Ser-Val-Gln | KIDZ-12 | >1 mM | — | >20 mM | >20 mM | 134 |
| Pro-Phe-Met-Ser-Val-Gln | KIDZ-13 | >4 mM | — | >20 mM | >20 mM | 135 |
| Pro-Thr-Arg-Ser-Val-Gln | KIDZ-14 | 400–800 | — | — | >20 mM | 136 |
| Pro-Map-Aph-Ser-Val-Gln | KIDZ-15 | 110 | — | >20 mM | >20 mM | 137 |
| Phe-Pro-Phe-Phe(4NH$_2$)-aldehyde | KITSD-1 | 27 | — | — | — | 138 |
| Val-Phe-Phe(4NH$_2$)-aldehyde | KITDS-2 | 160 | — | — | — | 139 |
| Pro-Phe(4NH$_2$)-CO-COOCH$_3$ | KITDS-3 | 18 | — | — | — | 140 |
| Pro-Phe(4NH$_2$)-COH-COOCH$_3$ | KITDS-5 | >5 mM | — | — | — | 141 |

Example 7

Transport Across Model Membranes

Figure 4:
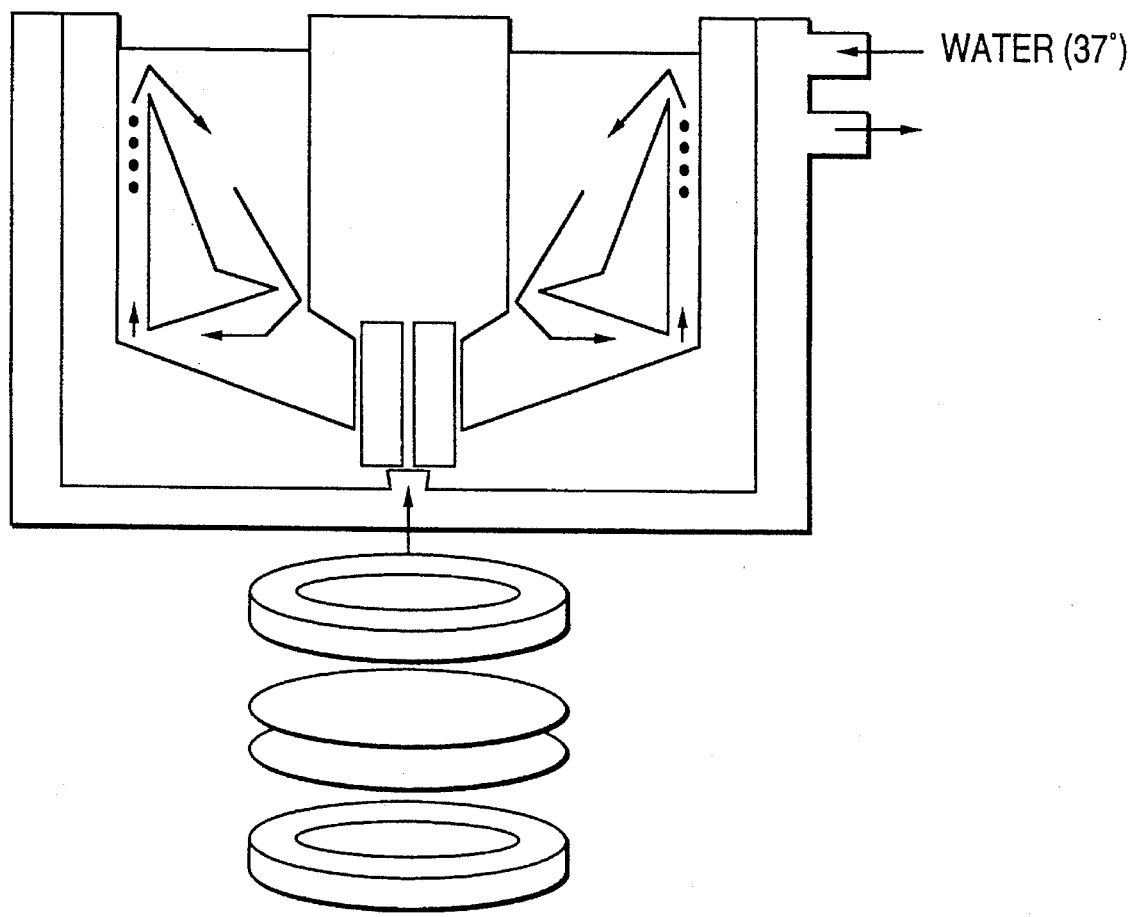
FIG. 4 Using Chamber used to measure $P_e$ values for peptide analogs.
Figure 5A:
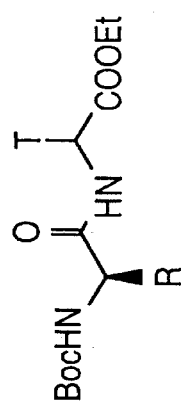
FIG. 5 Cyclic dipeptides used as model peptides in transport studies.
Figure 5B:
Figure 5C:
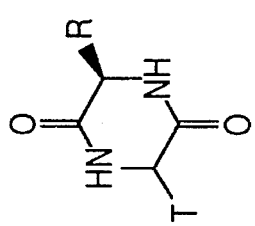
Figure 5D:
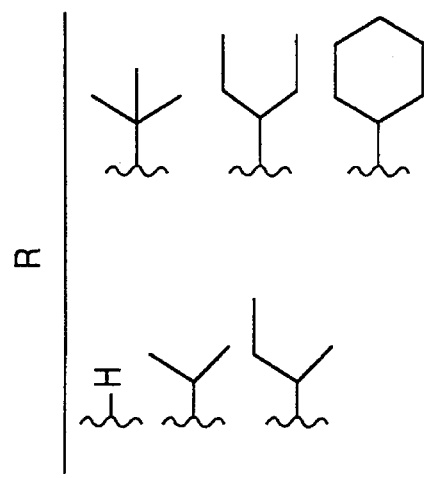

Studies on how changes in lipophilicity and size affect the rate at which peptides cross model membranes were performed. In these studies, the rate at which radioactive peptides cross from the serosal to the mucosal side of model membranes (FIG. 4) was measured. The model membranes are a human gut cell carcinoma line (T$_{84}$) which is grown on collagen coated Nucleopore membranes until the resistance mimics that of the human gut (1500 Ωcm$^{-2}$). This cell line has been used extensively to study peptide absorption.

Cyclic dipeptides (FIG. 5) are used as models for oligopeptide transport because they are relatively easy to synthesize in labeled form, resistant to degradative processes in the body, and cross membranes by diffusion (the same way that tetra- and larger peptides do). The molecular volume of the cyclic dipeptides was calculated using CHARMm and the lipophilicity (K$_{o/w}$) was both calculated (MedChem 3.53) and measured.

Results from these studies show that (1) the cyclic dipeptides cross the model membranes at rates directly proportional to concentration, (2) there is no side-to-side difference in the rate, and (3) the peptides are not degraded during transport which appears to occur by diffusion.

$$P_c = 19.7 \times K_{o/w} + 6.1 \quad (r^2, 0.99) \qquad (1)$$

Figure 6:
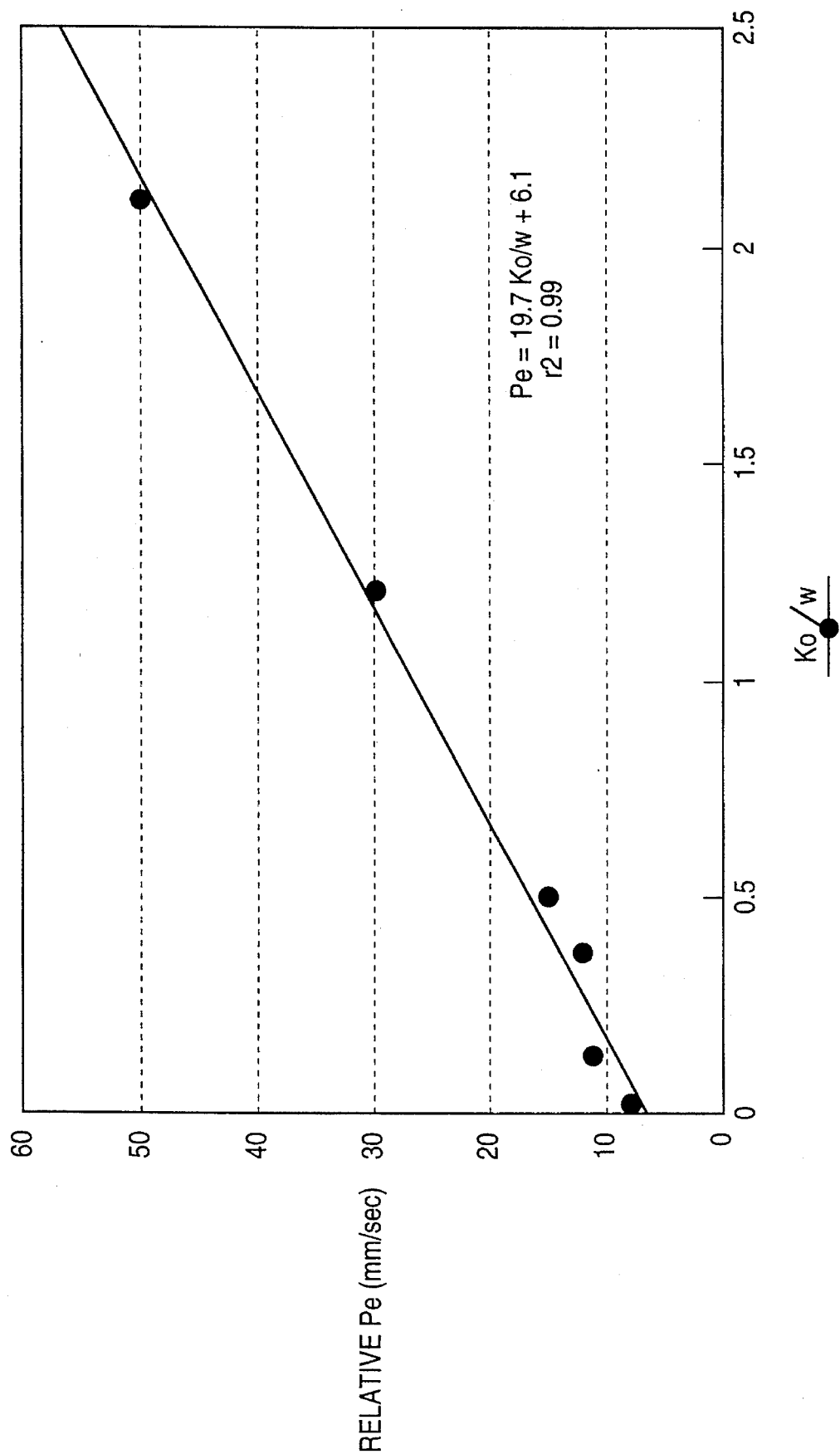
FIG. 6 Relationship between $P_e$ and $K_{O/W}$ for the passage of cyclic dipeptides across $T_{84}$ cell membranes.

This equation (Equation 1) gives the rate of passage of the peptides across the T$_{84}$ cell membrane as a function of lipophilicity. P$_c$ is the permeability coefficient. A plot of the data is shown in FIG. 6.

Figure 7:
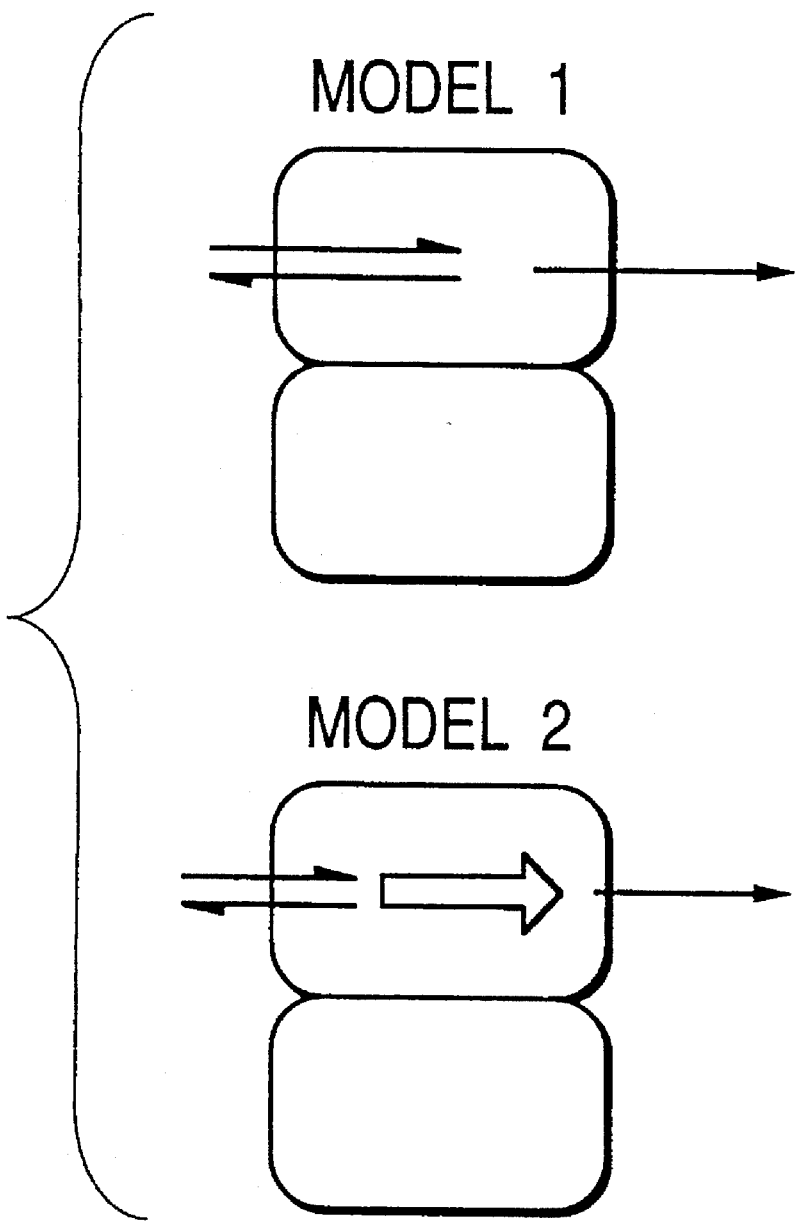
FIG. 7 Effect of the kallikrein antagonist on Toxin A intestinal secretion.

There are two competing models for the absorption of peptides. In the first, peptides reach an equilibrium between the mucosal chamber and the cell membrane. They then enter the serosal chamber at a rate proportional to their concentration in the membrane (FIG. 7, Model 1).

In the second Model, peptides reach equilibrium between the mucosal chamber and the surface layers of the cell membrane, but then diffuse across the cell membrane before they can enter the serosal chamber. The diffusion is highly dependent on the volume of the peptide because, it is thought, macromolecules dissolved in the cell membrane interrupt passage (non-Stokesain diffusion, FIG. 7, Model 2).

The results are consistent with Model 1. Diffusion across the membrane is proportional to the partition coefficient (K$_{o/w}$) of the cyclic peptides. Data from these experiments gives a poorer fit to the general equation derived from Model 2.

The studies discussed above can be used directly to increase the absorption of peptides from the human gut. Artusson and Karlsson determined the P$_e$ values for a series of drugs, including peptides, and then correlated their values with data from various drug compounds on the absorption of these compounds in vivo. An equation which quantitatively relates their data (Equation 2) and allows the percent absorption to be calculated from P$_e$.

$$\% \text{ Absorbance} = \frac{100}{1 + 10^{1.4 - 3.5 \log P_e}} \qquad (2)$$

Combining Equations 1 and 2 yields and equation which relates percent absorption to lipophilicity for various cyclic dipeptides.

Example 8

In Vivo Studies

Toxin A was prepared from sterile culture supernates of *Clostridium difficile* strain 10463 by ammonium sulfate precipitation and anion-exchange chromatography as described by I. Oh-Ishi (Infect. Immun. 40:691–95, 1983). Purity and biological activity were also verified. Male New Zealand rabbits weighing two kilograms were used in all studies. Animals were fasted overnight before the study, but were provided with water ad libitum. After catheterization of an ear vein, animals were anesthetized by intravenous injection of sodium pentobarbital. The abdomen was opened by a midline incision and 10 centimeter (cm) long segments of the distal ileum were ligated to form closed ileal loops. For each animal, two 10 cm loops were formed with at least a 5 cm distance between loops. Before injection of ileal loops, each group of rabbits received intravenous 100 mls of either normal saline alone or normal saline containing 50 mg of the kallikrein antagonist, KIDZ-6 for the entire period of the experiment (4 hours). Each loop was then injected with 1.0 ml of 50 mM Tris buffer (pH 7.4) containing 20 ug of toxin A or buffer alone (control). The abdomen was then closed in two layers and animals were maintained under light anesthesia with pentobarbital intravenously, and their body temperatures maintained at 37° C. to 38° C. with a heating lamp. After 4 hours rabbits were killed with a bolus of pentobarbital and loops were removed, weighed and measured, and loop contents aspirated and assayed for volume. Full-thickness sections of ileal loops were fixed in formalin and processed for light microscopy (not shown). Secretion of fluid was estimated as a weight to length ratio (mg/cm) of each loop essentially as described by I. Oh-Ishi (Infect. Immun. 40:691–95, 1983), which is shown in FIG. 8. Statistical analysis were performed using the GB-STAT professional statistics software program (Dynamic Microsystems, Inc., Maryland). Analysis of variance with protected t-tests were used for the inter-group comparisons.

Injection of 20 ug of toxin A into the 10 cm loops of saline treated animals caused a 2.4-fold increase of fluid secretion as compared to control loops treated with buffer ($p<0.01$). Injection of the same amount of toxin A into loops of animals treated with the kallikrein antagonist KIDZ-6 resulted in significant inhibition of secretion (by 61.6%, $p<0.05$). "n" indicates number of loops tested per group.

Other embodiments and uses of the invention will be apparent to those skilled in the art from consideration of the specification and practice of the invention disclosed therein. It is intended that the specification and examples be considered exemplary only, with the true scope and spirit of the invention being indicated by the following claims.

---

We claim:

1. A pharmaceutical composition comprised of a substrate analog of tissue kallikrein with a length of less than 20 amino acids containing a sequence which corresponds to positions 388 to 390 of human kininogen, and which has a 4-amino phenylalanine (Phe(4NH$_2$)), or a similar modified amino acid, corresponding to position 389, and a pharmaceutically acceptable carrier.

2. The pharmaceutical composition of claim 1 wherein the sequence comprises naturally occurring, non-naturally occurring, or chemically synthesized amino acids, amino acid derivatives, modified amino acids, or combinations thereof.

3. The pharmaceutical composition of claim 1 wherein the sequence corresponds to positions 386 to 392 of kininogen.

4. The pharmaceutical composition of claim 1 wherein the sequence is between three to ten amino acids in length.

5. The pharmaceutical composition of claim 1 wherein the sequence is (SEQ. ID. NO.: 128):

Pro-Phe-Phe(4NH$_2$)-Ser-Val-Gln-NH$_2$.

6. The pharmaceutical composition of claim 1 wherein the substrate analog specifically inhibits the activity of pig, rabbit or human tissue kallikrein.

7. The pharmaceutically composition of claim 1 wherein the pharmaceutically acceptable carrier is selected from the group consisting of water, oil, alcohol, saline, glycerol, polysaccharide, starch, and a combination thereof.

8. The pharmaceutical composition of claim 1 wherein the substrate analog has a $K_I$ of less than 1.0 micromole.

9. The pharmaceutical composition of claim 1 wherein the substrate analog has a $K_I$ of 0.1 micromoles.

10. A method for the treatment of inflammation in a patient comprised of administering to the patient a therapeutically effective amount of a pharmaceutical composition containing a substrate analog of tissue kallikrein with a length of less than 20 amino acids, containing a sequence which corresponds to positions 388 to 390 of human kininogen, and which has a 4-aminophenylalanine (Phe(4NH$_2$)), or a similar modified amino acid, corresponding to position 389.

11. The method of claim 10 wherein the sequence corresponds to positions 386 to 392 of kininogen.

12. The method of claim 10 wherein the pharmaceutical composition is administered orally, parenterally, sublingually, rectally, enterally, by pulmonary absorption, or by topical application.

13. The method of claim 10 wherein the patient is a human.

14. The method of claim 10 wherein the sequence is (SEQ. ID. NO. 128):

Pro-Phe-Phe(4NH$_2$)-Ser-Val-Gln-NH$_2$.

15. A method for the treatment of hypotension in a human comprised of administering to the human a therapeutically effective amount of a pharmaceutical composition comprised of a substrate analog of tissue kallikrein with a length of less than 20 amino acids, containing a sequence which corresponds to at least positions 388 to 390 of human kininogen, and which has a 4-aminophenylalanine (Phe(4NH$_2$)), or a similar modified amino acid, corresponding to position 389.

16. A method for the treatment of pain in a human comprised of administering to the human a therapeutically effective amount of a pharmaceutical composition comprised of a substrate analog of tissue kallikrein with a length of less than 20 amino acids, containing a sequence which corresponds to at least positions 388 to 390 of human kininogen, and which has a 4-amino phenylalanine (Phe(4NH$_2$)), or a similar modified amino acid, corresponding to position 389.

17. A method for the treatment of edema in a human comprised of administering to the human a therapeutically effective amount of a pharmaceutical composition comprised of a substrate analog of tissue kallikrein with a length of less than 20 amino acids, containing a sequence which corresponds to at least positions 388 to 390 of human kininogen, and which has a 4-aminophenylalanine (Phe(4NH$_2$)), or a similar modified amino acid, corresponding to position 389.

18. A peptide which specifically inhibits the activity of tissue kallikrein with a length of less than 20 amino acids, containing a sequence which corresponds to at least positions 389 to 390 of human kininogen, and which has a 4-amino phenylalanine (Phe(4NH$_2$)), or a structurally similar residue, corresponding to position 389.

19. The pharmaceutical composition of claim 1 wherein the peptide is readily absorbed through a biological membrane.

20. The pharmaceutical composition of claim 19 wherein the biological membrane is epithelium of a gastrointestinal tract.

* * * * *

SEQUENCE LISTING ( 1 ) GENERAL INFORMATION:

( i i i ) NUMBER OF SEQUENCES: 141

( 2 ) INFORMATION FOR SEQ ID NO:1:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:1:

Arg Ser Val Gln
1

( 2 ) INFORMATION FOR SEQ ID NO:2:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:2:

Phe Arg Ser Val Gln
1         5

( 2 ) INFORMATION FOR SEQ ID NO:3:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY:
  ( B ) LOCATION:

( x i ) SEQUENCE DESCRIPTION: SEQ ID NO:3:

Pro Phe Arg Ser Val Gln
1         5

( 2 ) INFORMATION FOR SEQ ID NO:4:

(i) SEQUENCE CHARACTERISTICS:
   (A) LENGTH: 7 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:4:

Ser Pro Phe Arg Ser Val Gln
1               5

(2) INFORMATION FOR SEQ ID NO:5:

(i) SEQUENCE CHARACTERISTICS:
   (A) LENGTH: 6 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:5:

Xaa Phe Arg Ser Val Gln
1               5

(2) INFORMATION FOR SEQ ID NO:6:

(i) SEQUENCE CHARACTERISTICS:
   (A) LENGTH: 6 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:6:

Xaa Phe Arg Ser Val Gln
1               5

(2) INFORMATION FOR SEQ ID NO:7:

(i) SEQUENCE CHARACTERISTICS:
   (A) LENGTH: 5 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:7:

Pro Phe Arg Ser Val
1               5

(2) INFORMATION FOR SEQ ID NO:8:

(i) SEQUENCE CHARACTERISTICS:
   (A) LENGTH: 7 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:8:

Pro Phe Arg Ser Val Gln Val
1               5

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Leu Met Lys Arg Pro Pro
1               5
```

( 2 ) INFORMATION FOR SEQ ID NO:10:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Met Lys Arg Pro
1
```

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Leu Met Lys Arg Pro
1               5
```

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Ser Leu Met Lys Arg Pro
1               5
```

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Xaa Phe Arg Ser Val Gln
1               5
```

( 2 ) INFORMATION FOR SEQ ID NO:14:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

Xaa  Phe  Arg  Ser  Val  Gln
    1                        5

( 2 ) INFORMATION FOR SEQ ID NO:15:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

Pro  Phe  Arg  Ser
    1

( 2 ) INFORMATION FOR SEQ ID NO:16:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

Ser  Pro  Phe  Arg
    1

( 2 ) INFORMATION FOR SEQ ID NO:17:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

Ser  Pro  Phe  Arg  Ser
    1                    5

( 2 ) INFORMATION FOR SEQ ID NO:18:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

Pro  Phe  Arg  Ser  Ser  Arg
    1                    5

( 2 ) INFORMATION FOR SEQ ID NO:19:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

Pro  Phe  Arg  Ser  Val  Arg
    1                         5

( 2 ) INFORMATION FOR SEQ ID NO:20:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Thr  Ser  Leu  Met  Lys  Arg  Pro
    1                       5

( 2 ) INFORMATION FOR SEQ ID NO:21:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

Thr  Ser  Leu  Met  Lys  Arg  Pro  Pro
    1                       5

( 2 ) INFORMATION FOR SEQ ID NO:22:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

Leu  Met  Lys  Arg
    1

( 2 ) INFORMATION FOR SEQ ID NO:23:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

Gly  Pro  Xaa  Lys  Ala  Arg  Ile  Ile (2) INFORMATION FOR SEQ ID NO:24:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

Gly  Pro  Xaa  Lys  Ala  Arg  Ile
    1                      5

(2) INFORMATION FOR SEQ ID NO:25:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

Gly  Pro  Xaa  Lys  Ala  Arg
    1                      5

(2) INFORMATION FOR SEQ ID NO:26:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Gly  Pro  Xaa  Lys  Ala
    1                      5

(2) INFORMATION FOR SEQ ID NO:27:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

Gly  Pro  Xaa  Lys
    1

(2) INFORMATION FOR SEQ ID NO:28:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site ( B ) LOCATION: 4

( x i ) SEQUENCE DESCRIPTION: SEQ ID NO:28:

Val Tyr Gly Cys Arg
1               5

( 2 ) INFORMATION FOR SEQ ID NO:29:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 4

( x i ) SEQUENCE DESCRIPTION: SEQ ID NO:29:

Tyr Gly Gly Cys Arg
1               5

( 2 ) INFORMATION FOR SEQ ID NO:30:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 3

( x i ) SEQUENCE DESCRIPTION: SEQ ID NO:30:

Gly Gly Cys Arg
1

( 2 ) INFORMATION FOR SEQ ID NO:31:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2

( x i ) SEQUENCE DESCRIPTION: SEQ ID NO:31:

Gly Cys Arg
1

( 2 ) INFORMATION FOR SEQ ID NO:32:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:32:

```
        Gly  Cys  Arg  Pro  Cys  Lys
        1                   5
```

( 2 ) INFORMATION FOR SEQ ID NO:33:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

```
        Gly  Cys  Arg  Gly  Pro  Cys  Lys
        1                   5
```

( 2 ) INFORMATION FOR SEQ ID NO:34:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:34:

```
        Gly  Cys  Arg  Gly  Gly  Pro  Cys  Lys
        1                   5
```

( 2 ) INFORMATION FOR SEQ ID NO:35:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1

( x i ) SEQUENCE DESCRIPTION: SEQ ID NO:35:

```
        Phe  Ser  Val  Gln
        1
```

( 2 ) INFORMATION FOR SEQ ID NO:36:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 3

( x i ) SEQUENCE DESCRIPTION: SEQ ID NO:36:

```
        Pro  Phe  Phe  Xaa
        1
```

( 2 ) INFORMATION FOR SEQ ID NO:37:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 3

( x i ) SEQUENCE DESCRIPTION: SEQ ID NO:37:

Pro Phe Phe Xaa Val Gln
1               5

( 2 ) INFORMATION FOR SEQ ID NO:38:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 4

( x i ) SEQUENCE DESCRIPTION: SEQ ID NO:38:

Gly Pro Xaa Phe Ala Arg Ile Ile
1               5

( 2 ) INFORMATION FOR SEQ ID NO:39:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:39:

Ser Val Glu Val
1

( 2 ) INFORMATION FOR SEQ ID NO:40:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 3

( x i ) SEQUENCE DESCRIPTION: SEQ ID NO:40:

Pro Phe Arg
1

( 2 ) INFORMATION FOR SEQ ID NO:41:

( i ) SEQUENCE CHARACTERISTICS:
        ( A ) LENGTH: 6 amino acids
        ( B ) TYPE: amino acid -continued ( C ) STRANDEDNESS: single
    ( D ) TOPOLOGY: linear ( i i ) MOLECULE TYPE: peptide ( x i ) SEQUENCE DESCRIPTION: SEQ ID NO:41:

Pro Phe Arg Leu Val Arg
 1        5

( 2 ) INFORMATION FOR SEQ ID NO:42:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:42:

Gly Pro Xaa Arg Ala Arg Ile Ile
 1        5

( 2 ) INFORMATION FOR SEQ ID NO:43:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:43:

Gly Pro Phe Arg Ala Arg Ile Ile
 1        5

( 2 ) INFORMATION FOR SEQ ID NO:44:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:44:

Gly Pro Xaa Arg Ser Arg Ile Ile
 1        5

( 2 ) INFORMATION FOR SEQ ID NO:45:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:45:

Gly Pro Xaa Lys Ala Val Ile Ile
 1        5

( 2 ) INFORMATION FOR SEQ ID NO:46:

( i ) SEQUENCE CHARACTERISTICS:
    ( A ) LENGTH: 8 amino acids (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:46:

Ser Pro Phe Arg Ser Val Glu Val
    1               5

(2) INFORMATION FOR SEQ ID NO:47:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:47:

Ser Pro Phe Arg Ser Val
    1               5

(2) INFORMATION FOR SEQ ID NO:48:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:48:

Phe Arg Val Glu Val
    1               5

(2) INFORMATION FOR SEQ ID NO:49:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:49:

Phe Arg Ser Val
    1

(2) INFORMATION FOR SEQ ID NO:50:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:50:

Ala Arg Ile Ile
    1

(2) INFORMATION FOR SEQ ID NO:51:

(i) SEQUENCE CHARACTERISTICS:

(A) LENGTH: 9 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:51:

Thr Gly Pro Xaa Lys Ala Arg Ile Ile
1               5

(2) INFORMATION FOR SEQ ID NO:52:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:52:

Xaa Lys Ala Arg Ile Ile
1               5

(2) INFORMATION FOR SEQ ID NO:53:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:53:

Lys Ala Arg Ile Ile
1               5

(2) INFORMATION FOR SEQ ID NO:54:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:54:

Gly Phe Arg Ser Val Gln
1               5

(2) INFORMATION FOR SEQ ID NO:55:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1

(xi) SEQUENCE DESCRIPTION: SEQ ID NO:55:

Ala Phe Arg Ser Val Gln
1               5

( 2 ) INFORMATION FOR SEQ ID NO:56:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1

( x i ) SEQUENCE DESCRIPTION: SEQ ID NO:56:

Xaa  Phe  Arg  Ser  Val  Gln
1                          5

( 2 ) INFORMATION FOR SEQ ID NO:57:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1

( x i ) SEQUENCE DESCRIPTION: SEQ ID NO:57:

Val  Phe  Arg  Ser  Val  Gln
1                          5

( 2 ) INFORMATION FOR SEQ ID NO:58:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1

( x i ) SEQUENCE DESCRIPTION: SEQ ID NO:58:

Gly  Phe  Arg  Ser  Val  Gln
1                          5

( 2 ) INFORMATION FOR SEQ ID NO:59:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1

( x i ) SEQUENCE DESCRIPTION: SEQ ID NO:59:

Ile  Phe  Arg  Ser  Val  Gln ( 2 ) INFORMATION FOR SEQ ID NO:60:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1

( x i ) SEQUENCE DESCRIPTION: SEQ ID NO:60:

Xaa Phe Arg Ser Val Gln
1                5

( 2 ) INFORMATION FOR SEQ ID NO:61:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1

( x i ) SEQUENCE DESCRIPTION: SEQ ID NO:61:

Ile Phe Arg Ser Val Gln
1                5

( 2 ) INFORMATION FOR SEQ ID NO:62:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1

( x i ) SEQUENCE DESCRIPTION: SEQ ID NO:62:

Xaa Phe Arg Ser Val Gln
1                5

( 2 ) INFORMATION FOR SEQ ID NO:63:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2

( x i ) SEQUENCE DESCRIPTION: SEQ ID NO:63:

```
Pro  Phe  Arg  Ser  Val  Gln
1                   5
```

(2) INFORMATION FOR SEQ ID NO:64:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2

(xi) SEQUENCE DESCRIPTION: SEQ ID NO:64:

```
Pro  Phe  Arg  Ser  Val  Gln
1                   5
```

(2) INFORMATION FOR SEQ ID NO:65:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2

(xi) SEQUENCE DESCRIPTION: SEQ ID NO:65:

```
Pro  Phe  Arg  Ser  Val  Gln
1                   5
```

(2) INFORMATION FOR SEQ ID NO:66:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2

(xi) SEQUENCE DESCRIPTION: SEQ ID NO:66:

```
Pro  Phe  Arg  Ser  Val  Gln
1                   5
```

(2) INFORMATION FOR SEQ ID NO:67:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2

(xi) SEQUENCE DESCRIPTION: SEQ ID NO:67:

```
    Pro  Phe  Arg  Ser  Val  Gln
    1                 5
```

(2) INFORMATION FOR SEQ ID NO:68:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2

(xi) SEQUENCE DESCRIPTION: SEQ ID NO:68:

```
    Pro  Phe  Arg  Ser  Val  Gln
    1                 5
```

(2) INFORMATION FOR SEQ ID NO:69:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2

(xi) SEQUENCE DESCRIPTION: SEQ ID NO:69:

```
    Pro  Phe  Arg  Ser  Val  Gln
    1                 5
```

(2) INFORMATION FOR SEQ ID NO:70:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2

(xi) SEQUENCE DESCRIPTION: SEQ ID NO:70:

```
    Pro  Phe  Arg  Ser  Val  Gln
    1                 5
```

(2) INFORMATION FOR SEQ ID NO:71:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2

( x i ) SEQUENCE DESCRIPTION: SEQ ID NO:71:

Pro Phe Arg Ser Val Gln
1               5

( 2 ) INFORMATION FOR SEQ ID NO:72:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2

( x i ) SEQUENCE DESCRIPTION: SEQ ID NO:72:

Pro Phe Arg Ser Val Gln
1               5

( 2 ) INFORMATION FOR SEQ ID NO:73:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2

( x i ) SEQUENCE DESCRIPTION: SEQ ID NO:73:

Pro Phe Arg Ser Val Gln
1               5

( 2 ) INFORMATION FOR SEQ ID NO:74:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2

( x i ) SEQUENCE DESCRIPTION: SEQ ID NO:74:

Pro Phe Arg Ser Val Gln
1               5

( 2 ) INFORMATION FOR SEQ ID NO:75:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2

( x i ) SEQUENCE DESCRIPTION: SEQ ID NO:75:

Pro Phe Arg Ser Val Gln
1               5

( 2 ) INFORMATION FOR SEQ ID NO:76:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 2

( x i ) SEQUENCE DESCRIPTION: SEQ ID NO:76:

Pro Phe Arg Ser Val Gln
1               5

( 2 ) INFORMATION FOR SEQ ID NO:77:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1

( x i ) SEQUENCE DESCRIPTION: SEQ ID NO:77:

Ile Phe Arg Ser Val Gln
1               5

( 2 ) INFORMATION FOR SEQ ID NO:78:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 2

( x i ) SEQUENCE DESCRIPTION: SEQ ID NO:78:

Pro Phe Arg Ser Val Gln
1               5

( 2 ) INFORMATION FOR SEQ ID NO:79:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site ( B ) LOCATION: 2

( x i ) SEQUENCE DESCRIPTION: SEQ ID NO:79:

Pro Phe Arg Ser Val Gln
1               5

( 2 ) INFORMATION FOR SEQ ID NO:80:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:80:

Pro Xaa Arg Ser Val Gln
1               5

( 2 ) INFORMATION FOR SEQ ID NO:81:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:81:

Pro Xaa Arg Ser Val Gln
1               5

( 2 ) INFORMATION FOR SEQ ID NO:82:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:82:

Pro Xaa Arg Ser Val Gln
1               5

( 2 ) INFORMATION FOR SEQ ID NO:83:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2

( x i ) SEQUENCE DESCRIPTION: SEQ ID NO:83:

Pro Xaa Arg Ser Val Gln
1               5

( 2 ) INFORMATION FOR SEQ ID NO:84:

( i ) SEQUENCE CHARACTERISTICS:

(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 2

(xi) SEQUENCE DESCRIPTION: SEQ ID NO:84:

Pro Xaa Arg Ser Val Gln
1               5

(2) INFORMATION FOR SEQ ID NO:85:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 2

(xi) SEQUENCE DESCRIPTION: SEQ ID NO:85:

Pro Xaa Arg Ser Val Gln
1               5

(2) INFORMATION FOR SEQ ID NO:86:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 2

(xi) SEQUENCE DESCRIPTION: SEQ ID NO:86:

Pro Phe Arg Ser Val Gln
1               5

(2) INFORMATION FOR SEQ ID NO:87:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:87:

Pro Xaa Arg Ser Val Gln
1               5

(2) INFORMATION FOR SEQ ID NO:88:

(i) SEQUENCE CHARACTERISTICS:
(A) LENGTH: 6 amino acids
(B) TYPE: amino acid
(C) STRANDEDNESS: single ( D ) TOPOLOGY: linear ( i i ) MOLECULE TYPE: peptide ( x i ) SEQUENCE DESCRIPTION: SEQ ID NO:88:

```
Pro  Trp  Arg  Ser  Val  Gln
1                   5
```

( 2 ) INFORMATION FOR SEQ ID NO:89:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2

( x i ) SEQUENCE DESCRIPTION: SEQ ID NO:89:

```
Pro  Trp  Arg  Ser  Val  Gln
1                   5
```

( 2 ) INFORMATION FOR SEQ ID NO:90:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2

( x i ) SEQUENCE DESCRIPTION: SEQ ID NO:90:

```
Pro  Xaa  Arg  Ser  Val  Gln
1                   5
```

( 2 ) INFORMATION FOR SEQ ID NO:91:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2

( x i ) SEQUENCE DESCRIPTION: SEQ ID NO:91:

```
Pro  Xaa  Arg  Ser  Val  Gln
1                   5
```

( 2 ) INFORMATION FOR SEQ ID NO:92:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide (xi) SEQUENCE DESCRIPTION: SEQ ID NO:92:

Pro Phe Arg Asn Val Gln
1               5

(2) INFORMATION FOR SEQ ID NO:93:

(i) SEQUENCE CHARACTERISTICS:
     (A) LENGTH: 6 amino acids
     (B) TYPE: amino acid
     (C) STRANDEDNESS: single
     (D) TOPOLOGY: linear (ii) MOLECULE TYPE: peptide (xi) SEQUENCE DESCRIPTION: SEQ ID NO:93:

Pro Phe Arg Asp Val Gln
1               5

(2) INFORMATION FOR SEQ ID NO:94:

(i) SEQUENCE CHARACTERISTICS:
     (A) LENGTH: 6 amino acids
     (B) TYPE: amino acid
     (C) STRANDEDNESS: single
     (D) TOPOLOGY: linear (ii) MOLECULE TYPE: peptide (xi) SEQUENCE DESCRIPTION: SEQ ID NO:94:

Pro Phe Arg Arg Val Gln
1               5

(2) INFORMATION FOR SEQ ID NO:95:

(i) SEQUENCE CHARACTERISTICS:
     (A) LENGTH: 6 amino acids
     (B) TYPE: amino acid
     (C) STRANDEDNESS: single
     (D) TOPOLOGY: linear (ii) MOLECULE TYPE: peptide (xi) SEQUENCE DESCRIPTION: SEQ ID NO:95:

Pro Phe Arg Cys Val Gln
1               5

(2) INFORMATION FOR SEQ ID NO:96:

(i) SEQUENCE CHARACTERISTICS:
     (A) LENGTH: 6 amino acids
     (B) TYPE: amino acid
     (C) STRANDEDNESS: single
     (D) TOPOLOGY: linear (ii) MOLECULE TYPE: peptide (ix) FEATURE:
     (A) NAME/KEY: Modified-site
     (B) LOCATION: 4

(xi) SEQUENCE DESCRIPTION: SEQ ID NO:96:

Pro Phe Arg Cys Val Gln
1               5

(2) INFORMATION FOR SEQ ID NO:97:

(i) SEQUENCE CHARACTERISTICS:
     (A) LENGTH: 6 amino acids (B) TYPE: amino acid
(C) STRANDEDNESS: single
(D) TOPOLOGY: linear (i i) MOLECULE TYPE: peptide (x i) SEQUENCE DESCRIPTION: SEQ ID NO:97:

Pro Phe Arg Gln Val Gln
1               5

(2) INFORMATION FOR SEQ ID NO:98:

(i) SEQUENCE CHARACTERISTICS:
    (A) LENGTH: 6 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:98:

Pro Phe Arg Xaa Val Gln
1               5

(2) INFORMATION FOR SEQ ID NO:99:

(i) SEQUENCE CHARACTERISTICS:
    (A) LENGTH: 6 amino acids
    (B) TYPE: amino acid
    (C) STRANDEDNESS: single
    (D) TOPOLOGY: linear (i i) MOLECULE TYPE: peptide (i x) FEATURE:
    (A) NAME/KEY: Modified-site
    (B) LOCATION: 4

(x i) SEQUENCE DESCRIPTION: SEQ ID NO:99:

Pro Phe Arg Cys Val Gln
1               5

(2) INFORMATION FOR SEQ ID NO:100:

(i) SEQUENCE CHARACTERISTICS:
    (A) LENGTH: 6 amino acids
    (B) TYPE: amino acid
    (C) STRANDEDNESS: single
    (D) TOPOLOGY: linear (i i) MOLECULE TYPE: peptide (i x) FEATURE:
    (A) NAME/KEY: Modified-site
    (B) LOCATION: 4

(x i) SEQUENCE DESCRIPTION: SEQ ID NO:100:

Pro Phe Arg Ser Val Gln
1               5

(2) INFORMATION FOR SEQ ID NO:101:

(i) SEQUENCE CHARACTERISTICS:
    (A) LENGTH: 6 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:101:

```
      Pro  Phe  Arg  Ala  Val  Gln
      1                   5
```

( 2 ) INFORMATION FOR SEQ ID NO:102:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:102:

```
      Pro  Phe  Arg  Thr  Val  Gln
      1                   5
```

( 2 ) INFORMATION FOR SEQ ID NO:103:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 4

( x i ) SEQUENCE DESCRIPTION: SEQ ID NO:103:

```
      Pro  Phe  Arg  Thr  Val  Gln
      1                   5
```

( 2 ) INFORMATION FOR SEQ ID NO:104:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 4

( x i ) SEQUENCE DESCRIPTION: SEQ ID NO:104:

```
      Pro  Phe  Arg  Asn  Val  Gln
      1                   5
```

( 2 ) INFORMATION FOR SEQ ID NO:105:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:105:

```
      Pro  Phe  Arg  Ser  Ser  Arg
      1                   5
```

( 2 ) INFORMATION FOR SEQ ID NO:106:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:106:

Val Phe Arg Asn Ser Arg
1               5

(2) INFORMATION FOR SEQ ID NO:107:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:107:

Val Phe Arg Asn Asn Arg
1               5

(2) INFORMATION FOR SEQ ID NO:108:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:108:

Pro Phe Arg Ser Arg Gln
1               5

(2) INFORMATION FOR SEQ ID NO:109:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:109:

Pro Phe Arg Asn Arg Gln
1               5

(2) INFORMATION FOR SEQ ID NO:110:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:110:

Pro Arg Arg Ser Val Gln
1               5

(2) INFORMATION FOR SEQ ID NO:111:

( i ) SEQUENCE CHARACTERISTICS:
   ( A ) LENGTH: 6 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Modified-site
   ( B ) LOCATION: 1

( x i ) SEQUENCE DESCRIPTION: SEQ ID NO:111:

Xaa Phe Arg Xaa Val Gln
1               5

( 2 ) INFORMATION FOR SEQ ID NO:112:

( i ) SEQUENCE CHARACTERISTICS:
   ( A ) LENGTH: 6 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:112:

Arg Phe Arg Asn Arg Gln
1               5

( 2 ) INFORMATION FOR SEQ ID NO:113:

( i ) SEQUENCE CHARACTERISTICS:
   ( A ) LENGTH: 6 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:113:

Phe Phe Arg Asn Arg Gln
1               5

( 2 ) INFORMATION FOR SEQ ID NO:114:

( i ) SEQUENCE CHARACTERISTICS:
   ( A ) LENGTH: 6 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:114:

Phe Phe Arg Asn Arg Gln
1               5

( 2 ) INFORMATION FOR SEQ ID NO:115:

( i ) SEQUENCE CHARACTERISTICS:
   ( A ) LENGTH: 6 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:115:

Val Phe Arg Ser Arg Gln
1               5

(2) INFORMATION FOR SEQ ID NO:116:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:116:

Val Phe Arg Asn Arg Gln
1               5

(2) INFORMATION FOR SEQ ID NO:117:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 5

(xi) SEQUENCE DESCRIPTION: SEQ ID NO:117:

Val Phe Arg Asn Arg Gly
1               5

(2) INFORMATION FOR SEQ ID NO:118:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:118:

Val Phe Arg Asn Lys Gln
1               5

(2) INFORMATION FOR SEQ ID NO:119:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 5

(xi) SEQUENCE DESCRIPTION: SEQ ID NO:119:

Val Phe Arg Asn Arg Gln
1               5

(2) INFORMATION FOR SEQ ID NO:120:

(i) SEQUENCE CHARACTERISTICS:

(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 3

(xi) SEQUENCE DESCRIPTION: SEQ ID NO:120:

Val Phe Arg Asn Xaa Gln
1               5

(2) INFORMATION FOR SEQ ID NO:121:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 3

(ix) FEATURE:
(A) NAME/KEY: Modified-site
(B) LOCATION: 5

(xi) SEQUENCE DESCRIPTION: SEQ ID NO:121:

Val Phe Arg Asn Arg Gln
1               5

(2) INFORMATION FOR SEQ ID NO:122:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:122:

Pro Cys Lys Ala Arg Ile
1               5

(2) INFORMATION FOR SEQ ID NO:123:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:123:

Phe Arg Ser Val Glu Val
1               5

(2) INFORMATION FOR SEQ ID NO:124:

(i) SEQUENCE CHARACTERISTICS:
(A) LENGTH: 6 amino acids
(B) TYPE: amino acid
(C) STRANDEDNESS: single (D) TOPOLOGY: linear (ii) MOLECULE TYPE: peptide (xi) SEQUENCE DESCRIPTION: SEQ ID NO:124:

Pro Phe Lys Ser Val Gln
1               5

(2) INFORMATION FOR SEQ ID NO:125:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:125:

Pro Phe Xaa Ser Val Gln
1               5

(2) INFORMATION FOR SEQ ID NO:126:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:126:

Pro Phe Xaa Ser Val Gln
1               5

(2) INFORMATION FOR SEQ ID NO:127:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:127:

Pro Phe Xaa Ser Val Gln
1               5

(2) INFORMATION FOR SEQ ID NO:128:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:128:

Pro Phe Xaa Ser Val Gln
1               5

(2) INFORMATION FOR SEQ ID NO:129:

(i) SEQUENCE CHARACTERISTICS:
    (A) LENGTH: 6 amino acids
    (B) TYPE: amino acid (C) STRANDEDNESS: single
(D) TOPOLOGY: linear (ii) MOLECULE TYPE: peptide (xi) SEQUENCE DESCRIPTION: SEQ ID NO:129:

Pro Phe Xaa Ser Val Gln
1               5

(2) INFORMATION FOR SEQ ID NO:130:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 3

(xi) SEQUENCE DESCRIPTION: SEQ ID NO:130:

Pro Phe Lys Ser Val Gln
1               5

(2) INFORMATION FOR SEQ ID NO:131:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 3

(xi) SEQUENCE DESCRIPTION: SEQ ID NO:131:

Pro Phe Xaa Ser Val Gln
1               5

(2) INFORMATION FOR SEQ ID NO:132:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:132:

Pro Phe Xaa Ser Val Gln
1               5

(2) INFORMATION FOR SEQ ID NO:133:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site -continued (B) LOCATION: 3

(xi) SEQUENCE DESCRIPTION: SEQ ID NO:133:

Pro Phe Xaa Ser Val Gln
1               5

(2) INFORMATION FOR SEQ ID NO:134:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:134:

Pro Phe His Ser Val Gln
1               5

(2) INFORMATION FOR SEQ ID NO:135:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:135:

Pro Phe Met Ser Val Gln
1               5

(2) INFORMATION FOR SEQ ID NO:136:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:136:

Pro Thr Arg Ser Val Gln
1               5

(2) INFORMATION FOR SEQ ID NO:137:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:137:

Pro Xaa Xaa Ser Val Gln
1               5

(2) INFORMATION FOR SEQ ID NO:138:

(i) SEQUENCE CHARACTERISTICS:
    (A) LENGTH: 4 amino acids
    (B) TYPE: amino acid
    (C) STRANDEDNESS: single
    (D) TOPOLOGY: linear ( i i ) MOLECULE TYPE: peptide ( i x ) FEATURE:
    ( A ) NAME/KEY: Modified-site
    ( B ) LOCATION: 4

( x i ) SEQUENCE DESCRIPTION: SEQ ID NO:138:

Phe Pro Phe Phe
1

( 2 ) INFORMATION FOR SEQ ID NO:139:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 3

( x i ) SEQUENCE DESCRIPTION: SEQ ID NO:139:

Val Phe Phe
1

( 2 ) INFORMATION FOR SEQ ID NO:140:

( i ) SEQUENCE CHARACTERISTICS:
        ( A ) LENGTH: 2 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2

( x i ) SEQUENCE DESCRIPTION: SEQ ID NO:140:

Pro Phe
1

( 2 ) INFORMATION FOR SEQ ID NO:141:

( i ) SEQUENCE CHARACTERISTICS:
        ( A ) LENGTH: 2 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2

( x i ) SEQUENCE DESCRIPTION: SEQ ID NO:141:

Pro Phe
1